United States Patent
Thielen

(10) Patent No.: US 6,616,680 B1
(45) Date of Patent: Sep. 9, 2003

(54) DISTAL PROTECTION AND DELIVERY SYSTEM AND METHOD

(76) Inventor: Joseph M. Thielen, 3027 Cameron Ave. SE., Buffalo, MN (US) 55313

( * ) Notice: Subject to any disclaimer, the term of this patent is extended or adjusted under 35 U.S.C. 154(b) by 0 days.

(21) Appl. No.: 09/703,887

(22) Filed: Nov. 1, 2000

(51) Int. Cl.⁷ .............................................. A61M 29/00
(52) U.S. Cl. ...................... 606/200; 606/194; 606/191
(58) Field of Search ................... 606/200, 191, 606/194, 198, 159, 195

(56) References Cited

U.S. PATENT DOCUMENTS

| | | | |
|---|---|---|---|
| 4,619,246 A | 10/1986 | Molgaard-Nielsen | 128/1 |
| 4,873,978 A | 10/1989 | Ginsburg | 128/345 |
| 4,969,891 A | 11/1990 | Gewertz | 606/200 |
| 5,133,733 A | 7/1992 | Rasmussen | 606/200 |
| 5,160,342 A | 11/1992 | Geger et al. | 606/200 |
| 5,769,816 A | 6/1998 | Barbut | 604/96 |
| 5,810,874 A | 9/1998 | Lefebure | 606/200 |
| 5,846,260 A | 12/1998 | Maahs | 606/200 |
| 5,910,154 A | 6/1999 | Tsugita | 606/200 |
| 5,928,261 A | 7/1999 | Ruiz | 606/200 |
| 5,941,896 A | 8/1999 | Kerr | 606/200 |
| 6,461,370 B1 * | 10/2002 | Gray et al. | 606/200 |
| 6,485,501 B1 * | 11/2002 | Green | 606/200 |
| 6,485,502 B2 * | 11/2002 | Don Michael et al. | 606/200 |

* cited by examiner

*Primary Examiner*—Danny Worrell

(57) ABSTRACT

A distal protection and delivery system is used to collect and remove embolic debris in the blood vessel. The system includes a guidewire, a filter assembly, and a distal introducer. The distal introducer can be positioned on a distal end of an introducer catheter or an angioplasty catheter or other interventional catheter. The guidewire has a small ferrule or locking mechanism fixed to it that does not affect the flexibility, torqueability, or trackability in comparison to standard guidewires. The introducer containing the filter assembly is advanced over the guidewire to a site distal to the lesion. Upon retraction of the guidewire proximally, the ferrule latches with an ejector latch of the filter assembly. Either advancement of the guidewire distally or retraction of the distal introducer proximally allows the filter assembly to be ejected from the distal introducer and into the blood vessel.

20 Claims, 32 Drawing Sheets

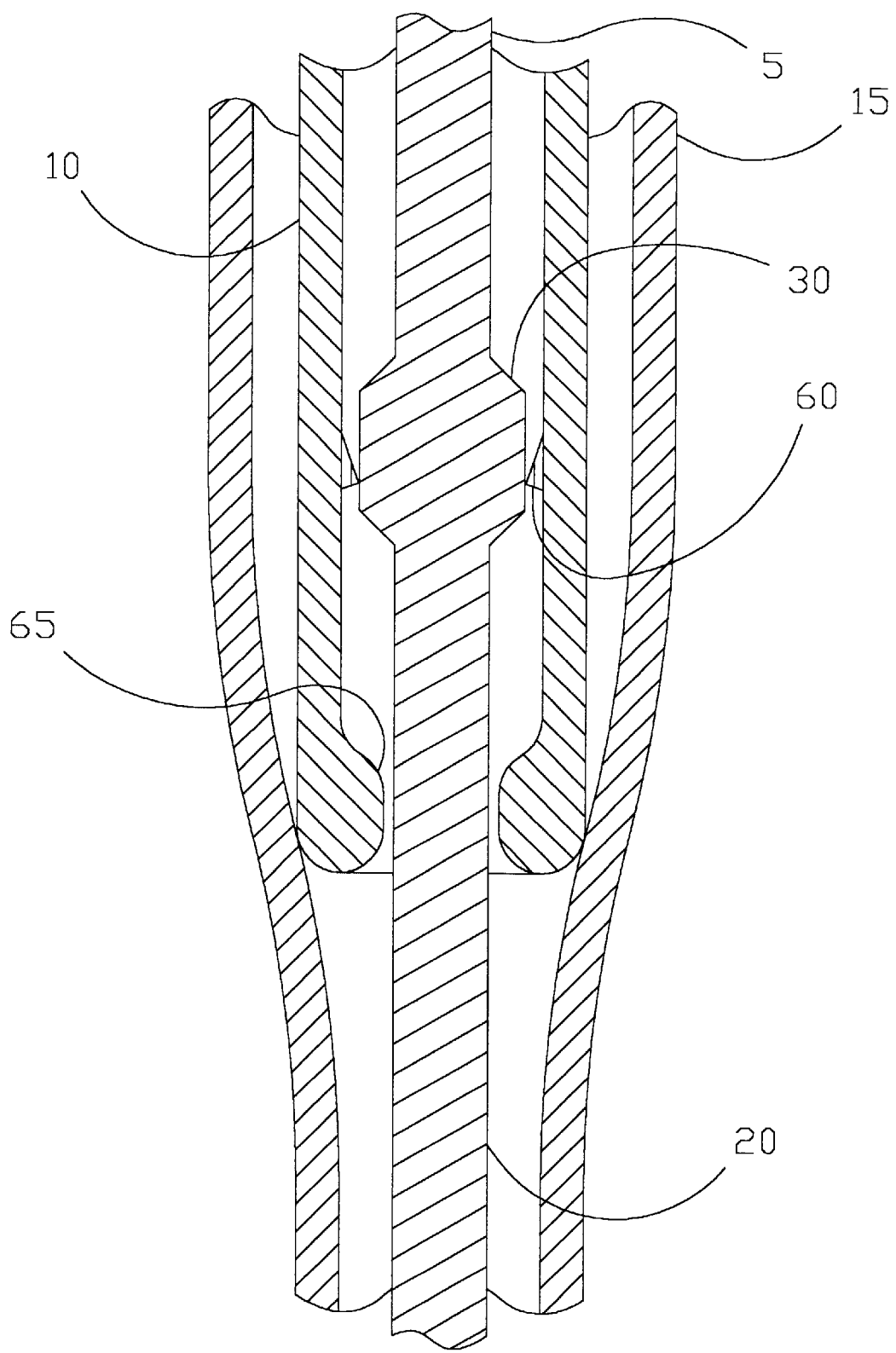

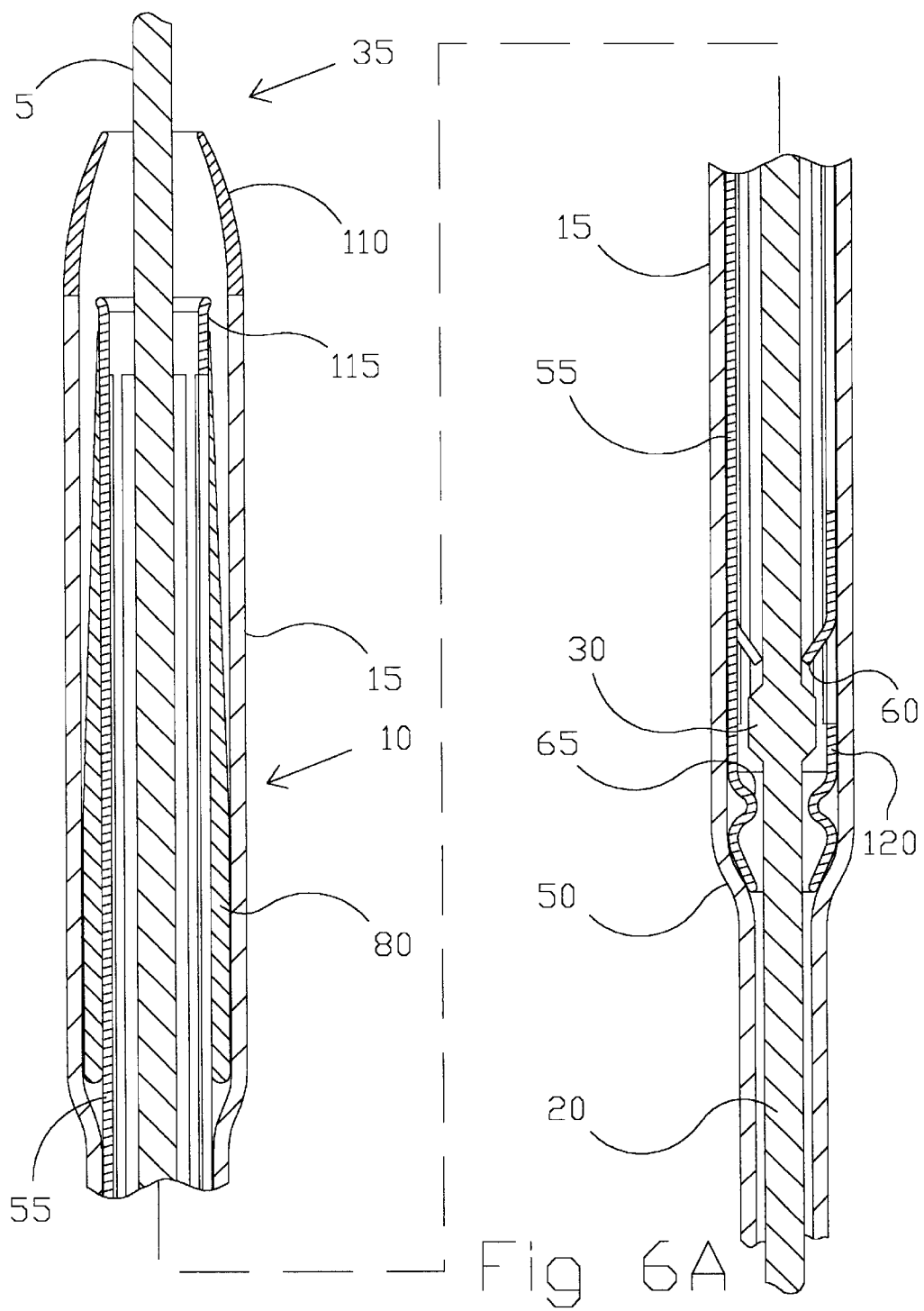

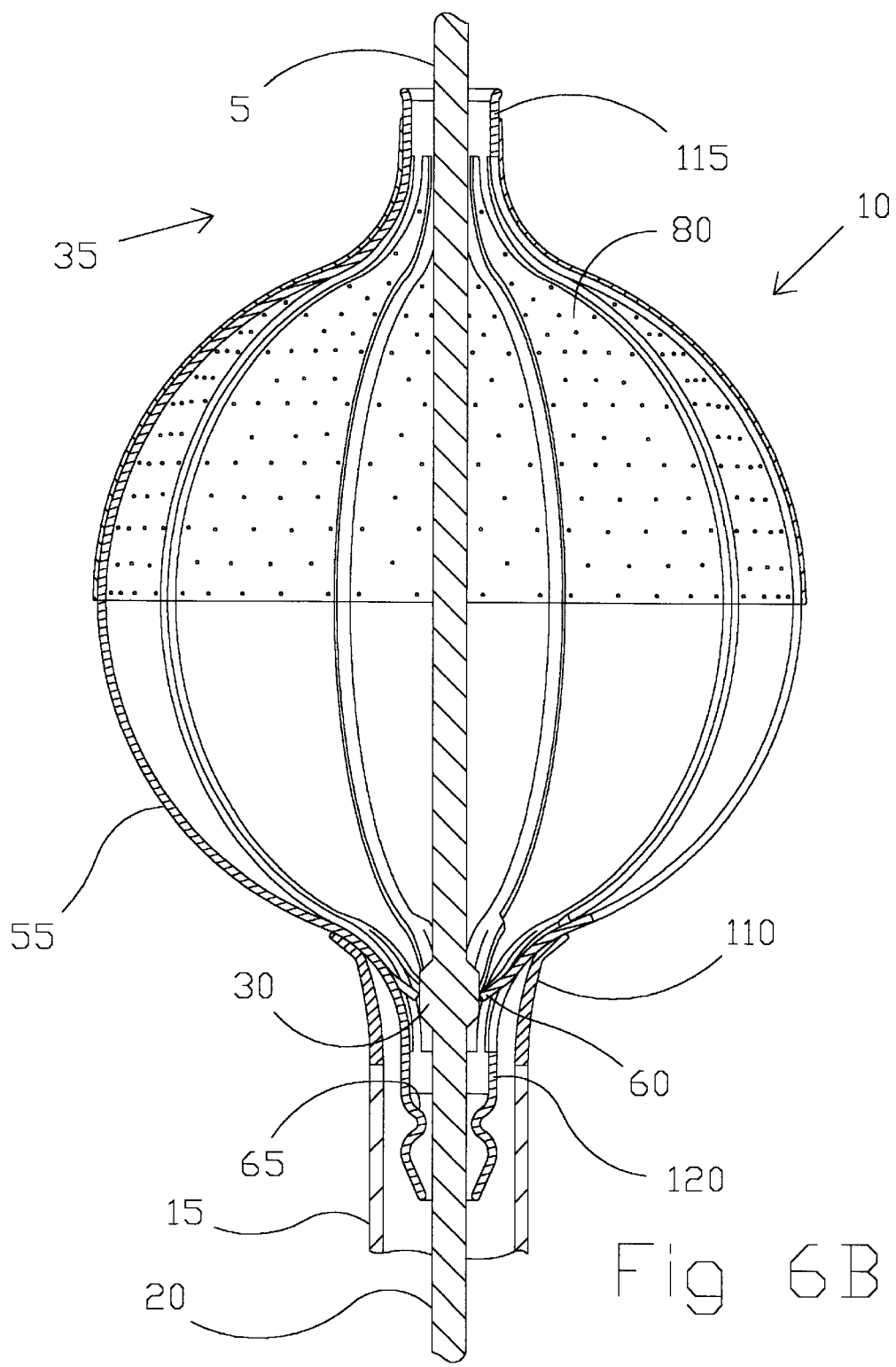

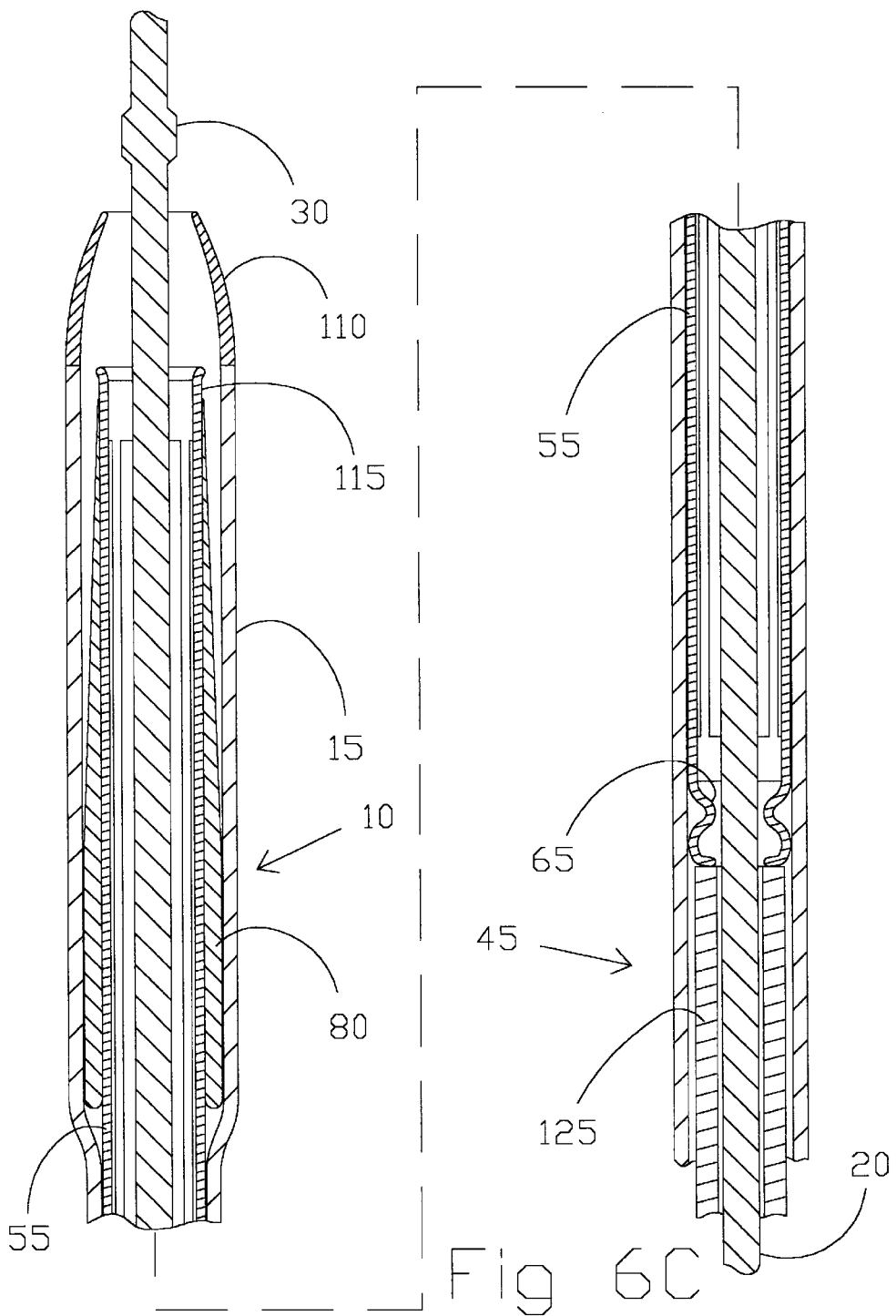

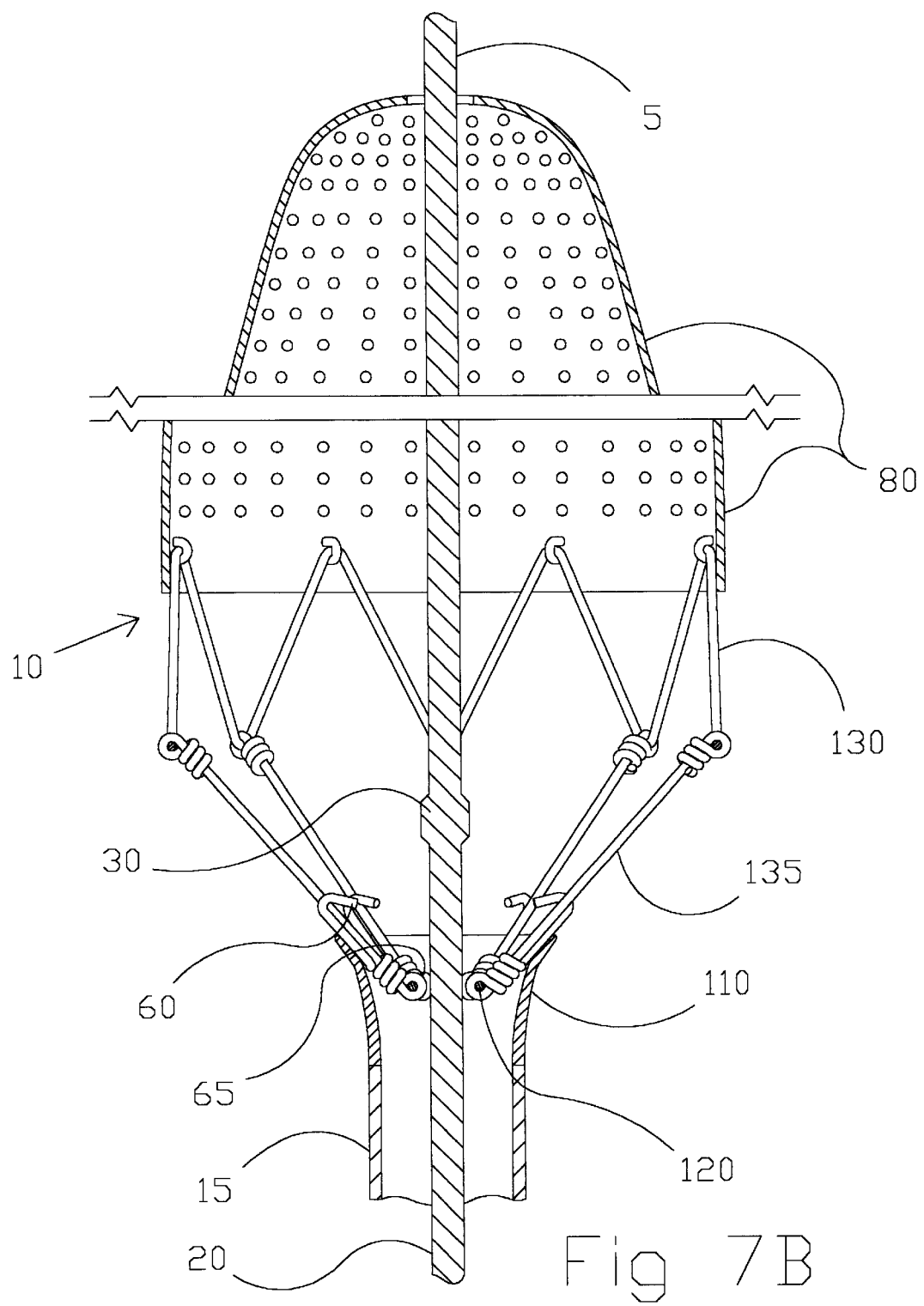

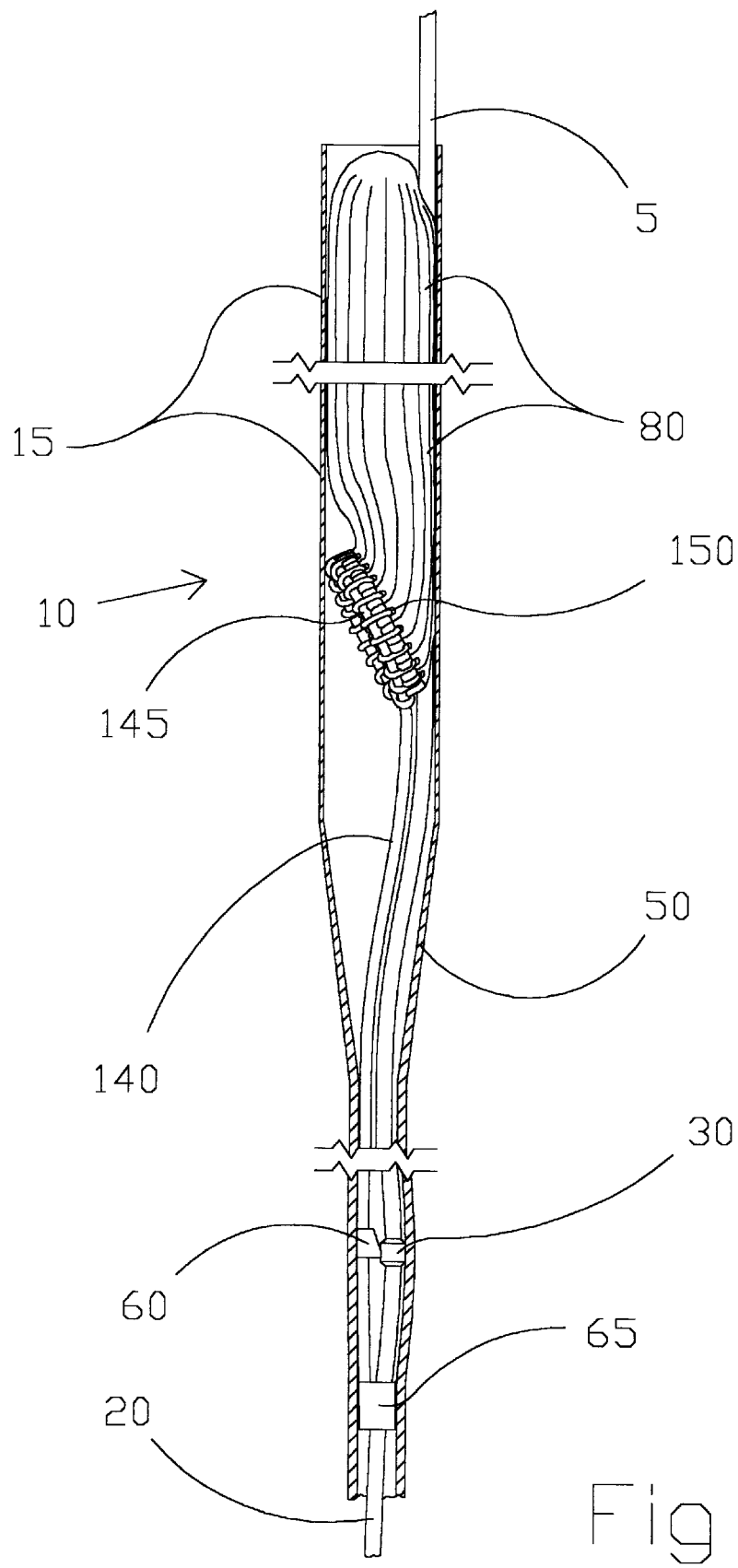

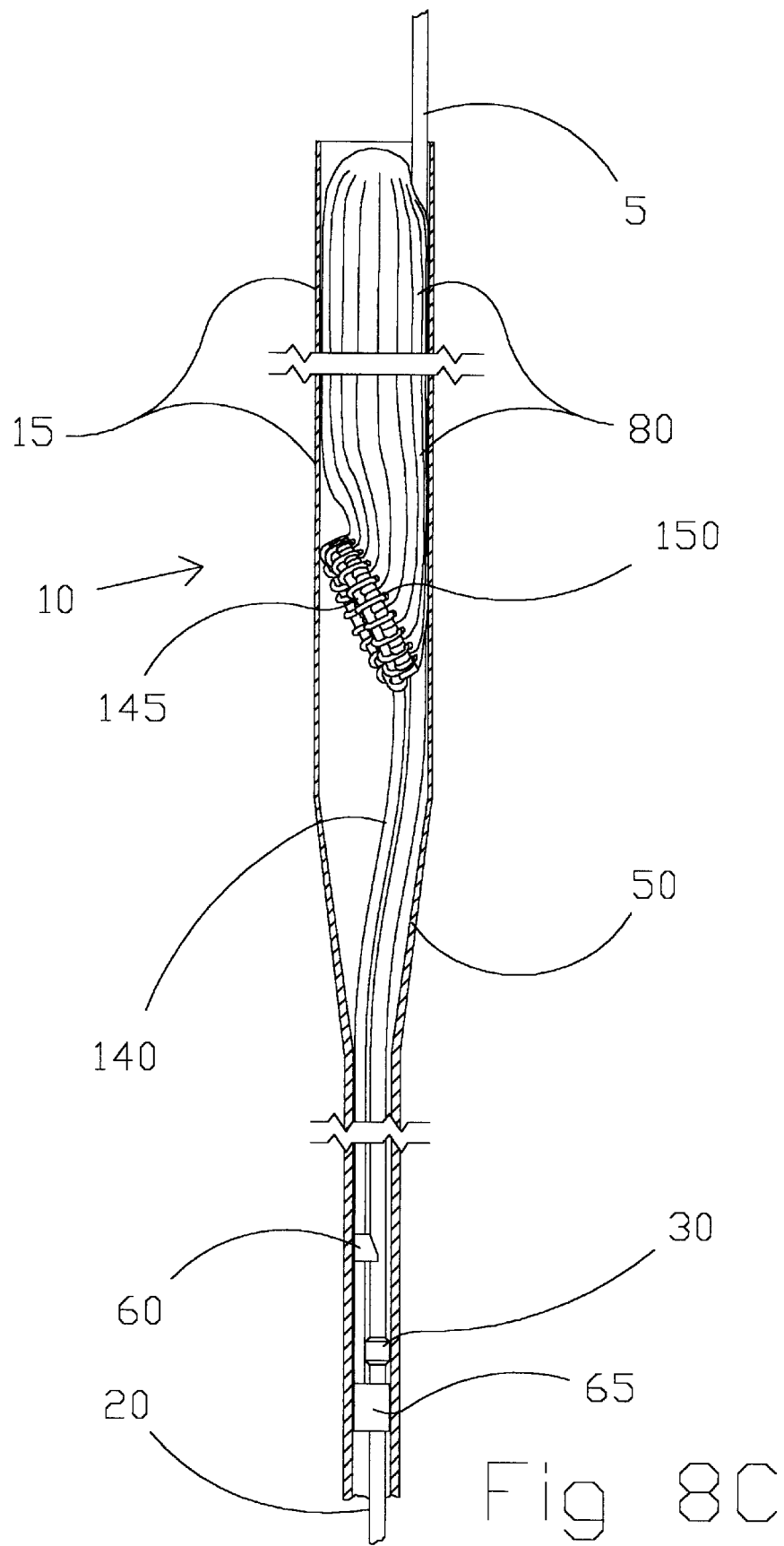

DISTAL PROTECTION AND DELIVERY SYSTEM AND METHOD

BACKGROUND OF THE INVENTION

1. Field of Invention

The present invention relates to a distal protection and delivery system that is placed using a guidewire in a tubular member of the human body that has a lesion or injury that requires diagnosis or therapy without allowing emboli to be released downstream. More specifically the invention relates to an intravascular system that is placed percutaneously into a blood vessel of the body that has a lesion to be treated by angioplasty, stent placement, atherectomy, thrombectomy, or other therapy, or diagnosis. The blood vessel to be treated can include the coronary, carotid, femoral, popliteal, or other vessel having a vascular lesion that requires interventional treatment. During treatment of such blood vessels, embolic debris can be embolized downstream causing blockage to distal capillary beds and arterioles. This vascular blockage results in reduced tissue perfusion and compromised tissue function. Placement of a distal protection device downstream of the treatment site can allow emboli to be collected and removed from the body rather than causing embolic injury. The distal protection and delivery system of the present invention includes a guidewire that can navigate tortuous blood vessel to reach the vessel lesion as easily as other standard prior art guidewires. The system also includes a filter assembly that is not attached to the guidewire and therefore can be delivered with an introducer to a site distal to the vessel lesion separately from the guidewire.

2. Description of Prior Art

Distal protection devices have been used in tubular vessels of the body including arteries and veins in order to prevent emboli such as thrombi, plaque, and other embolic debris from drifting downstream and causing distal tissue injury. Most distal protection devices have filters that are attached directly to the distal portion of a guidewire or to a portion of a catheter. Filter devices can sometimes be used during surgery, during percutaneous interventional procedures, and also filters can be implanted permanently into the body. The device of the present invention is intended for use during angioplasty or other interventional use.

Distal protection devices having a filter attached to a guidewire include the device of Tsugita (U.S. Pat. No. 5,910,154), Kerr (U.S. Pat. No. 5,941,896), Ruiz (U.S. Pat. No. 5,928,261), Reger (U.S. Pat. No. 5,160,342), and Ginsburg (U.S. Pat. No. 4,873,978). Tsugita describes a filter apparatus for treating stenosed blood vessels. The guidewire has a filter attached to it for capturing loose embolic material. The filter has an expansion frame having a filter mesh attached to it. One major difficulty with this type of device is that the guidewire cannot traverse a tortuous pathway in a blood vessel with a filter attached and with a holding tube surrounding the filter to hold it in the smaller diameter configuration. The filter along with the holding tube are very stiff and will restrict the ability of the guidewire from making tight turns into small vessels. Kerr describes a conically shaped filter with a porous fabric or a fine fiber mesh. Emboli from an angioplasty procedure are trapped by the filter and connecting loops can be drawn together to hold the emboli. This device shares similar disadvantages to the device of Tsugita. Ruiz describes a removable vascular filter and apparatus that is expanded within the vessel and held in place by a coiled-sheet stent portion with a magnetic band. When the coiled-sheet stent portion is released within the blood vessel, it uncoils to engage a wall of the vessel and deploys the filter element across the flow path. This device would be very stiff due to its configuration and would have much difficulty traversing a tortuous vascular pathway. Reger describes a filter device for use during angioplasty or atherectomy having a filter assembly mounted on a flexible catheter or guidewire. The device contains a filter element such as a polyester cloth that can be closed using a drawstring. A rotating motion can be used to twist the stocking filter to aid in containing the embolic material. This device has a filter permanently attached to the guidewire and will therefore have much greater stiffness than a standard guidewire, thereby limiting its access to smaller vessels and vessels with difficult conformation. Ginsburg describes a catheter device with a filter at the end of a wire that is entered percutaneously from the downstream side of the lesion. This device is extremely limited by virtue of reduced or nonexistent access to the blood vessel in most cases downstream of the lesion. This device also shares the difficulties associated with having a permanently attached filter that will result in a stiff device.

Lefebvre describes in U.S. Pat. No. 5,810,874 a filter catheter that is intended for long periods of use. It has strips that form a filter that can be detached from the connecting means into a blood vessel. This device is not intended to capture and remove emboli, however. This device depends upon the natural thrombolytic mechanisms of the body to break down thrombus or emboli that have been collected by the filter.

In U.S. Pat. No. 5,846,260 by Maahs a modular blood filter device is described that can be introduced into a blood vessel. The device consists of an arterial cannula with a modular filter device. The frame may be expanded to an enlarged condition to capture embolic material in a mesh filter and collapsed to a contracted condition and removed from the vessel. The device appears to be very mechanical, stiff, and cumbersome, and would not have efficient application to interventional procedures in vessels that require a soft and flexible catheter.

Barbut describes a device and method for filtering emboli generated from a blood oxygenator in U.S. Pat. No. 5,769,816. The device has an insertion tube, an umbrella frame for positioning and maintaining a mesh filter in position, and a means for opening the umbrella frame. An inflatable balloon is attached to the mesh filter. This device is much too stiff and awkward to be used in a percutaneous interventional application that requires a flexible catheter and guidewire.

Gewertz (U.S. Pat. No. 4,969,891) describes a filter member attached to a wire member that is intended to enter the jugular vein and be advanced to the vena cava. The device is easily replaceable and removable at the end of the procedure. This device does not retrieve the thromboemboli but rather depends upon the body to break down the emboli. This is a temporary filter to remove large clots in the venous system. It could not work to retrieve emboli in an interventional procedure.

Molgaard-Nielson (U.S. Pat. No. 4,619,246) and Rasmussen (U.S. Pat. No. 5,133,733) describe filters that are placed into a blood vessel such as a vein to block emboli. The device of Molgaard-Nielson is a wire filter mesh attached to a wire and could be implanted and then moved within one week. Emboli that have been trapped are not intended to be removed from the vasculature. Rasmussen describes a filter that is normally deployed in the vena cava via a catheter in a collapsed form and expands outward to capture emboli. This device is intended for implant and does not provide for means to remove any collected emboli.

SUMMARY OF THE INVENTION

The present distal protection and delivery system overcomes the disadvantages of other prior art distal protection devices. The present distal protection and delivery system does not have the filter assembly attached directly to the guidewire during insertion of the guidewire as it is with other prior art systems. Other prior art systems have attached their filter assembly directly to the guidewire and have compromised their ability to extend through difficult turns and reach some lesion sites due to the stiffness associated with the filter assembly and the introducer catheter. One component of the distal protection and delivery system of the present invention is a guidewire, another is a distal introducer, and another is a filter assembly. The guidewire component of the present invention can be formed with flexibility, trackability, and other structural features that are the same as other standard guidewires used for normal interventional procedures. Since the filter assembly is not permanently attached to the guidewire, the guidewire component of the present invention can extend through tortuous paths to reach and cross difficult lesions that require interventional treatment. Once the guidewire component of the present invention has reached the site of the lesion, an introducer catheter carrying a filter assembly in a nondeployed state is able to follow over the body or trunk of the guidewire to reach and cross the lesion. The filter assembly is then latched to a protrusion or ferrule located on the guidewire by an ejector latch on the filter assembly. The filter assembly is therein positioned on the guidewire and can be deployed into the blood vessel by advancing the guidewire distally or retracting the introducer proximally. The filter assembly undergoes an expansion from a smaller diameter of the introducer to the larger diameter of the blood vessel. A porous filter material located on a portion of the filter assembly serves to allow blood flow through the filter but restricts the flow of embolic material from passing distal to the filter assembly.

In one embodiment a latching of the filter assembly to the guidewire results in maintaining the positioning of the filter assembly with respect to the guidewire during deployment of the filter assembly and any axial movement of the guidewire can result in some movement of the filter assembly. In another embodiment latching of the filter assembly to the guidewire is only temporary (as long as) while the filter assembly is not deployed from the distal introducer. The filter assembly of this embodiment is unlatched upon deployment and the guidewire is free to move distally with respect to the filter assembly without affecting positioning of the filter assembly. In yet another embodiment an ejector tube is used to eject the filter assembly out of the introducer rather than using an ejector latch. In this embodiment the guidewire is free to move with respect to the filter assembly following deployment of the filter assembly into the blood vessel.

The filter material can be formed from a polymeric material or composite material that has holes of appropriate size to filter embolic debris drilled in it. Embolic debris can substantially range in size from about 10–1000 micrometers and can have the shape of flat plates or discs. Some embolic debris of a smaller diameter or thickness may be allowed to pass through the filter along with blood cellular elements which range in diameter from approximately 1–15 micrometers. Filter material can also be formed from cloth-like material such a woven polymeric, metallic, or composite materials. Other methods of forming the porous material include electrostatic spraying and extrusion of small polymeric filaments held together by solvent or thermal melt at crossover points. Another method of forming a porous thin filter material includes expanded polymeric material such as expanded polytetrafluoroethylene and expanded polypropylene.

With the filter assembly positioned in the blood vessel distal to the lesion the introducer can be removed from the blood vessel. An angioplasty catheter can then be introduced over the guidewire of the present invention. The present invention is primarily intended for and can be positioned in a coronary artery, a carotid artery, other neurovascular artery, a peripheral artery of the leg, or any other blood vessel that requires interventional treatment such as angioplasty and would benefit by a distal protection filter. Other therapeutic and diagnostic devices can also be advanced over the guidewire of the present invention such as stent delivery catheters, atherectomy catheters, thrombectomy catheters, angiography catheters, and other interventional catheters. During the use of such interventional catheters emboli are often generated from the plaque and deposit found on the vessel wall. These emboli can drift downstream if a distal protection device of the present invention is not positioned to capture the emboli distal to the lesion. Such emboli can block distal capillary beds and arterioles resulting in reduced tissue perfusion distal to the lesion. The presence of the filter assembly of the present invention will capture this embolic debris and allow the filter and embolic debris to be removed using the introducer of the present invention. In addition to use in the blood vessels of the body, the present invention could also be used in other tubular vessels of the body such as those found in the ureter, bladder, gall bladder, kidney, and other tubular vessels of the body.

Following the completion of all primary or adjunctive therapeutic or diagnostic procedures, the therapeutic or diagnostic catheters can be removed or retracted over the guidewire of the present invention. The introducer catheter can then be readvanced over the guidewire to a site of the filter assembly distal to the lesion in order to retrieve the filter assembly. The guidewire can be retracted proximally such that the locking mechanism of the guidewire interacts with a stop mechanism on the filter assembly and pulls the filter assembly proximally either partially or completely into the introducer catheter. The distal protection system of the present invention is then removed from the vasculature with the filter assembly containing the embolic debris.

The filter assembly of the present invention can have many conformations without changing the intent of the invention. In one embodiment the filter assembly is formed from Nitinol or other shape memory material support members that extend from a proximal band to a distal band that slidingly moves with respect to the guidewire. This embodiment of the filter assembly can be formed from a single shape memory or elastic metal tubular member that has been slotted by laser or other mechanical or chemical method to form the support members. Alternately, the filter assembly can be formed of wires made of an elastic or shape memory material that are attached to a proximal or distal band. The filter assembly is unable to escape distally from the guidewire due to a stop mechanism on the filter assembly that interfaces with a locking mechanism on the guidewire. The porous filter material is attached to the distal portion of these support members which hold the filter material outward against the vessel wall to prevent leakage of embolic debris around the perimeter of the filter or through the filter.

In another embodiment of the filter assembly a zig zag expandable ring is attached via support members to a proximal band. A porous filter material is attached to the distal end of the ring and forms a wind-sock form of embolic filter. In yet another embodiment for a filter assembly a Nitinol lasso is formed with a wind-sock like filter attached to it. Upon ejecting the filter assembly from the introducer, Nitinol wire is fed out to the loop allowing it to enlarge and come into contact with the vessel wall. In still yet another embodiment of the filter assembly two Nitinol wires connect together distally to form a single loop that is attached to a wind-sock like embolic filter. Upon ejection of the loop into the blood vessel the two Nitinol wires form an enlarged loop approximating the diameter of the blood vessel.

The distal protection and delivery system of the present invention can be operated as an over-the-wire system wherein the introducer catheter follows over a guidewire over substantially the entire length of the introducer catheter. In order to remove an over-the-wire introducer catheter while maintaining the position of the guidewire and filter assembly within the vessel distal to the lesion, an exchange length guidewire of the present invention of about 260–320 cm can be used. A long exchange length guidewire allows other over-the-wire therapeutic or diagnostic catheters to be placed over the guidewire and delivered to the site of the lesion and to remove them following their use. Alternately, an over-the-wire distal protection and delivery system having an over-the-wire introducer catheter containing the filter assembly can be initially loaded onto a shorter more standard length expandable guidewire of approximately 170–200 cm. This expandable guidewire can later be expanded if necessary to allow exchanges of over-the-wire catheters. The introducer and guidewire can be delivered percutaneously to a site that is proximal to the vascular lesion to be treated. For example, in treating a coronary lesion, the introducer and guidewire can be advanced through a guide catheter to a position near the coronary ostium. The guidewire can then be advanced across the lesion while the introducer catheter remains within the guide catheter. The distal introducer containing the filter assembly is then advanced over the guidewire to a position distal to the lesion. Deployment of the filter assembly is the same as described earlier. The guidewire is retracted proximally to latch the ejector latch of the filter assembly with the ferrule or locking mechanism located on the guidewire. The introducer is then withdrawn while maintaining the position of the guidewire to release the filter assembly and allow it to expand out to the diameter of the blood vessel. In order to remove the over-the-wire introducer from the vasculature without moving the distal end of the guidewire, a proximal extension guidewire of the present invention is attached by crimping or other mechanism to the proximal end of the expandable guidewire. This forms the expandable guidewire into an exchange length guidewire. Other catheters can be introduced over the extended guidewire and advanced to the lesion and can be removed from the vasculature over this guidewire. Following completion of interventional treatment the introducer catheter is reintroduced into the blood vessel the filter assembly is retracted into the distal introducer either partly or completely in a manner such that the filter membrane containing the embolic debris is retained within the distal introducer. The distal introducer, filter assembly, and guidewire can be removed from the vasculature along with the embolic debris that has been collected in the filter assembly.

Another embodiment of the distal protection and delivery system has an introducer catheter that is designed for rapid exchange with a distal introducer positioned at the distal end. In this embodiment the guidewire of the present invention can be of a standard length of approximately 170–200 cm and the introducer catheter provides passage for the guidewire through an intermediate portion of the catheter and the distal introducer. The filter assembly is positioned in the distal portion of the introducer and is deployed and retrieved back into the distal introducer in a manner similar to the other embodiments already described. The introducer catheter can be removed from the standard length guidewire while maintaining the position of the distal end of the guidewire in position across the lesion. Other rapid exchange therapeutic or diagnostic catheters can be delivered to the site of the lesion over the standard length guidewire of the present invention. The filter assembly can be removed from the vasculature using the initial rapid exchange introducer catheter that was used to deliver the filter assembly or an alternate introducer catheter of similar design but of a slightly larger diameter of the distal introducer to account for the embolic debris that has been collected during the interventional procedure.

Still yet another embodiment of the present invention has the distal introducer attached to the distal portion of an angioplasty catheter or other interventional catheter. In this embodiment the angioplasty catheter serves as an interventional therapeutic catheter and as an introducer catheter for the filter assembly. The angioplasty catheter can be a concentric design or a dual lumen construction design and the angioplasty catheter can be an over-the-wire design or a rapid exchange design. For example, the angioplasty catheter can have a guidewire tubing with a guidewire lumen for passage of a guidewire and an inflation lumen to inflate the dilatation balloon with contrast medium. Located distally to the dilatation balloon and attached to the guidewire tubing is located the distal introducer that was described in the previous embodiments. The distal introducer can be contiguous with the guidewire tube or it can be a separate tube which has been attached or bonded. This distal introducer contains the filter assembly. The guidewire of the present invention extends through the guidewire lumen of the angioplasty catheter and extends further distally through the filter assembly located in the distal introducer. Typical use of the device could include loading the guidewire of the present invention into the angioplasty catheter and distal introducer and advancing the guidewire and the angioplasty catheter with the distal introducer percutaneously into the vasculature. In the case of a coronary angioplasty or coronary stent placement, the angioplasty catheter with the distal introducer could be advanced within the guide catheter to the coronary ostium. In the case of carotid angioplasty or carotid stent placement, the angioplasty catheter with distal introducer could be advanced to the aortic arch or to the carotid ostium. The guidewire of the present invention is then advanced across the lesion to a site distal to the lesion. The angioplasty catheter with distal introducer is then advanced over the guidewire to a site distal to the vascular lesion. The guidewire can then be retracted to latch the ferrule or locking mechanism of the guidewire with the ejector latch of the filter assembly. Alternately the angioplasty catheter with distal introducer can be advanced distally while maintaining the position of the guidewire until the filter assembly has been latched. While maintaining the position of the guidewire the angioplasty catheter with distal introducer is withdrawn proximally a small distance to eject the filter assembly from the distal introducer and into the vessel. The filter assembly expands to form a seal with the vessel wall. The filter assembly can either remain latched to the guidewire or it can be designed to release from the guidewire allowing the guidewire to be moved distally while maintaining the position of the filter assembly within the blood vessel. The angioplasty catheter is then further withdrawn proximally until the dilatation balloon is positioned over the lesion and balloon dilatation of the lesion can proceed. If a stent is also located on the dilatation balloon, the stent can be implanted during the dilatation procedure. Following the angioplasty or other therapeutic procedure, the angioplasty catheter with distal introducer can be advanced distally a small distance and the guidewire can be retracted distally. The ferrule or locking mechanism on the guidewire will interface with the filter stop of the filter assembly and allow the filter assembly to be withdrawn back into the distal introducer. Embolic material generated by the angioplasty procedure or during stent placement will be collected in the filter assembly and will be held by the filter material of the filter assembly as it is withdrawn into the distal introducer. The angioplasty catheter with distal introducer along with the guidewire and filter assembly can then be removed from the blood vessel. It is to be understood that if an additional therapeutic or diagnostic catheter is needed following the initial angioplasty procedure, such as introducing another catheter for stent implantation, the angioplasty catheter with distal introducer can be removed while leaving the guidewire and filter assembly in place distal to the lesion. The additional therapeutic or diagnostic procedure can then be performed using the guidewire of the present invention that has been left in place and using the filter assembly that is also in place and fully deployed. Following the completion of the therapeutic or diagnostic procedure, the angioplasty catheter with distal introducer or another introducer catheter of present invention as was already described in a previous embodiment, can be used to retrieve the filter assembly by simply withdrawing the guidewire proximally into the distal introducer and pulling the filter assembly into the distal introducer. For those cases where only angioplasty is anticipated but it is desired to provide distal protection against embolic debris, this embodiment allows several benefits. First, a guidewire of standard flexibility, steerability, and trackability is first used to access the site of the lesion; the guidewire of the present invention does not have the filter assembly attached. Second, only one catheter is needed to both deliver the filter assembly and to perform the angioplasty procedure. Third, the same angioplasty catheter with distal introducer can then remove the filter assembly.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 2B is the sectional view of FIG. 2A in an intermediate condition;

FIG. 6A is a detailed sectional view of one embodiment of a distal protection and introducer system in a latched but undeployed condition;

FIG. 6B is the detailed sectional view of FIG. 6A in an intermediate condition;

FIG. 6C is a detailed sectional view of an embodiment similar to that of FIG. 6A in an undeployed condition but that uses an ejection tube to deploy;

FIG. 7B is the detailed partially sectioned view of FIG. 7A in a deployed condition;

FIG. 8B is the detailed partially sectioned view of FIG. 8A in the process of latching;

FIG. 8C is the detailed partially sectioned view of FIG. 8A in a latched condition;

DETAILED DESCRIPTION OF THE PREFERRED EMBODIMENTS

Figure 1A:
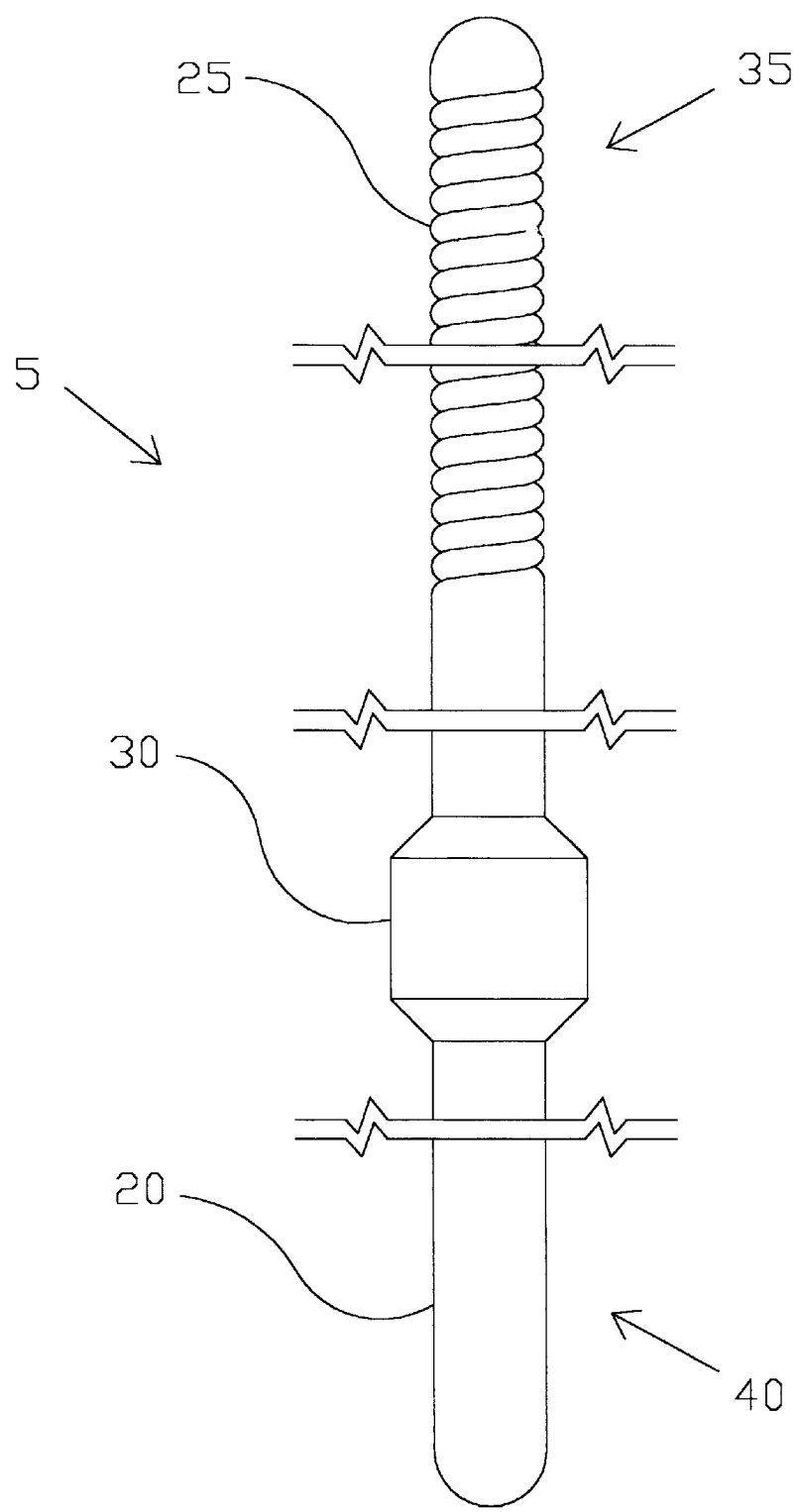
FIG. 1A is a plan view of a lockable guidewire.

One embodiment of the present invention is a distal protection and delivery system consisting of a lockable guidewire (5), a filter assembly (10), and a distal introducer (15) as shown in FIGS. 1A–1C and FIG. 2A. A view of the lockable guidewire (5) is shown in FIG. 1A. The diameter of the lockable guidewire trunk (20) for coronary, carotid, and small peripheral applications can range from 0.006 to 0.038 inches; a typical diameter range for the lockable guidewire (5) used in a coronary application can be 0.012 to 0.018 inches and a typical diameter range for carotid and neurovascular applications for the lockable guidewire (5) can be from 0.010 to 0.018 inches. Use of this lockable guidewire (5) for peripheral application such as in the vasculature of the leg typically could require a diameter of 0.014 to 0.038 inches. The lockable guidewire (5) of the present invention is delivered percutaneously to a remote site in the vasculature and has a distal coil (25) that allows the device to be advanced through the vasculature without causing vascular trauma. The lockable guidewire (5) provides a pathway over which additional devices such as angioplasty, atherectomy, thrombectomy, stent placement and other therapeutic or diagnostic catheters can follow and provide safe and effective treatment to an existing vascular lesion. The length of the lockable guidewire (5) can be long enough to allow an exchange of one therapeutic catheter such as an angioplasty catheter to be removed and replaced by another over-the-wire therapeutic catheter while maintaining the lockable guidewire (5) in place across the lesion. Such exchange length guidewires typically have a length of approximately 250–320 cm for coronary applications. The length of the lockable guidewire (5) can also be a standard length if it is to be used, for example, with rapid exchange devices that do not follow over-the-wire over their entire length. Such standard length guidewires typically have a length of approximately 150–220 cm for coronary applications. The lockable guidewire (5) has a ferrule (30) attached at a location generally closer to the distal end (35) than the proximal end (40) of the lockable guidewire (5). This ferrule (30) represents one example of a locking means located on the lockable guidewire (5) that provides the lockable guidewire (5) with its locking function as will be described later; it is understood that other locking means can equally provide such a locking function to the lockable guidewire (5). The ferrule (30) or other locking means is not allowed passage through the filter stop (65). The locking means such as a ferrule can be attached, for example, by crimping to any standard guidewire that is available for interventional procedures. Thus the physician could use his guidewire of choice to reach the site of the vessel lesion. The lockable guidewire (5) of the present invention can be torqued during advancement to reach the lesion without being affected by the filter assembly which is advanced to the lesion site afterwards.

Figure 1B:
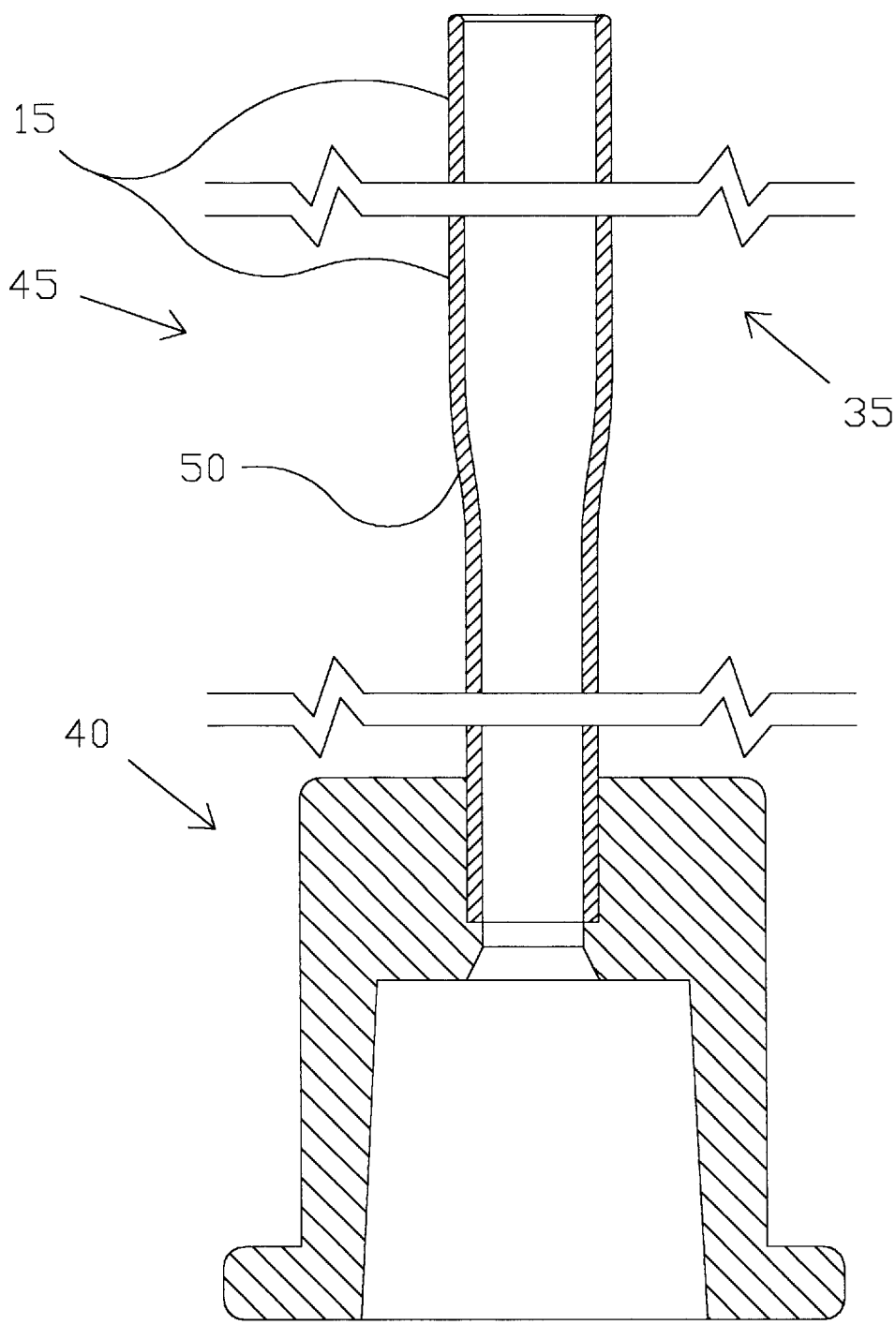
FIG. 1B is a sectional view of an introducer.

FIG. 1B is a view of the distal introducer (15) of this embodiment. It is formed of a flexible, thin wall material such as a polymeric material or a composite material such as a fiber or metallic reinforced polymeric material. The distal introducer (15) is joined either contiguously or by attachment to the distal end (35) of an introducer catheter (45) used to deliver the filter assembly (10) into the vasculature. The distal introducer (15) has a step (50) that provides a holding means to the filter assembly (10) preventing the filter assembly (10) from moving proximally beyond this step (50). It is understood that another stopping means could be used to prevent proximal movement of the filter assembly (10) within the distal introducer (15) without altering the present invention. The diameter of the distal introducer (15) is large enough to house the filter assembly (10). The distal introducer (15) can range from approximately 0.5–5 millimeters, and the diameter of the proximal end (40) of the introducer catheter (45) is large enough to house the lockable guidewire (5) and allow easy movement of the lockable guidewire (5) within it.

Figure 1C:
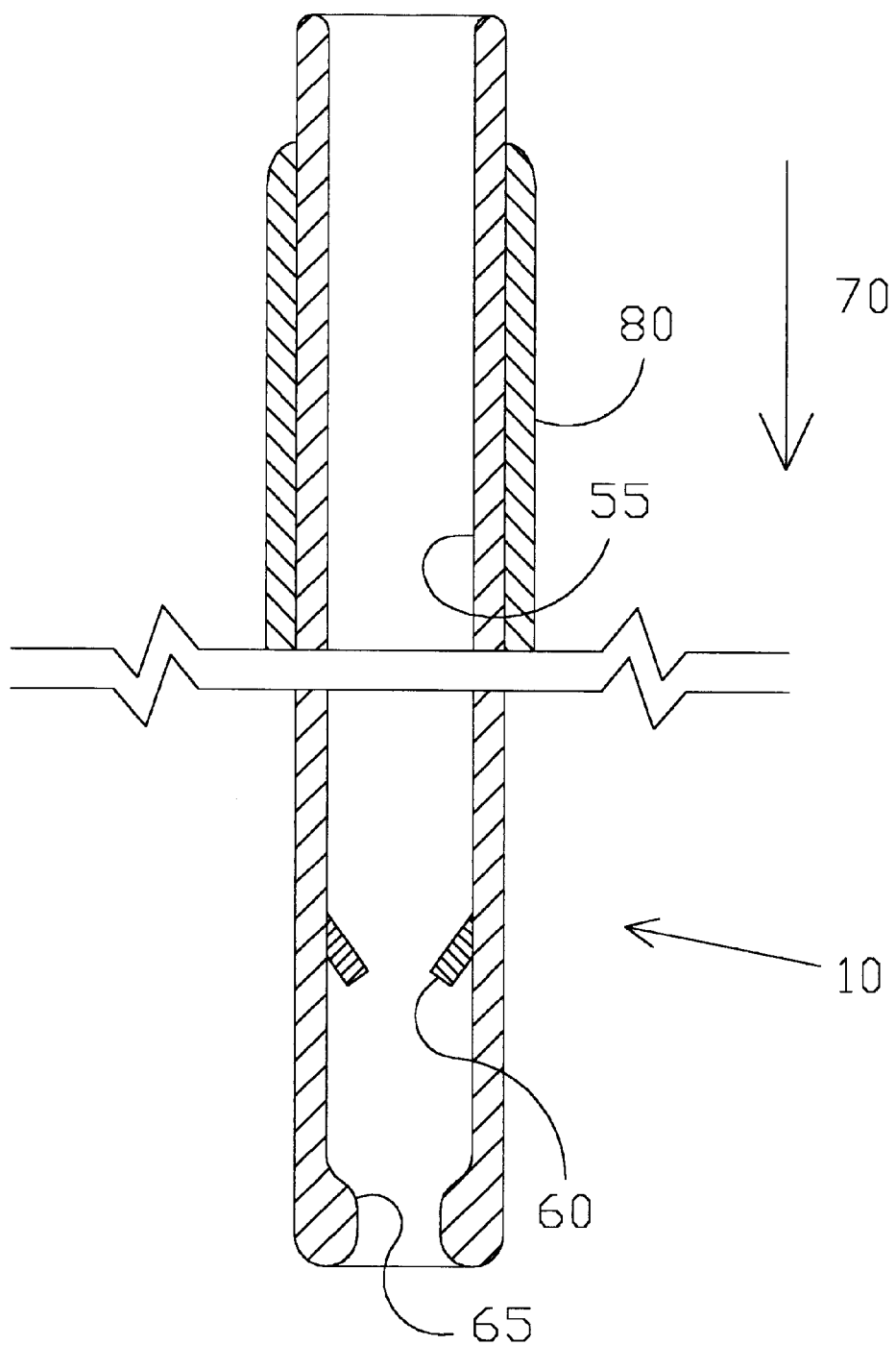
FIG. 1C is a sectional view of a filter assembly.

FIG. 1C is a view of the filter assembly (10) of the present embodiment in a nondeployed state. The filter assembly (10) has an expanding support structure (55) that can expand from its nondeployed state to an enlarged diameter or deployed state that is approximately the same diameter as the blood vessel which is being treated. The expanding support structure (55) can be formed out of Nitinol or other material with an elastic character or memory character that provides an outward force of the expanding support structure (55) against the vessel wall in its deployed state. An ejector latch (60) located on the filter assembly (10) in this embodiment serves as an ejector means in order to provide relative movement between the filter assembly (10) and the distal introducer (15) during removal or ejection of the filter from the distal introducer (15). A filter stop (65) located on the filter assembly (10) provides interface with the ferrule (30) of the lockable guidewire (5) such that the filter assembly (10) can be pulled by the lockable guidewire (5) in a proximal direction (70). The filter stop (65) does not restrict distal movement of the lockable guidewire trunk (20) with respect to the filter assembly (10). It is understood that another stop means can be used with the filter assembly (10) other than the filter stop (65) shown in FIG. 1C without changing the present invention.

Figure 2A:
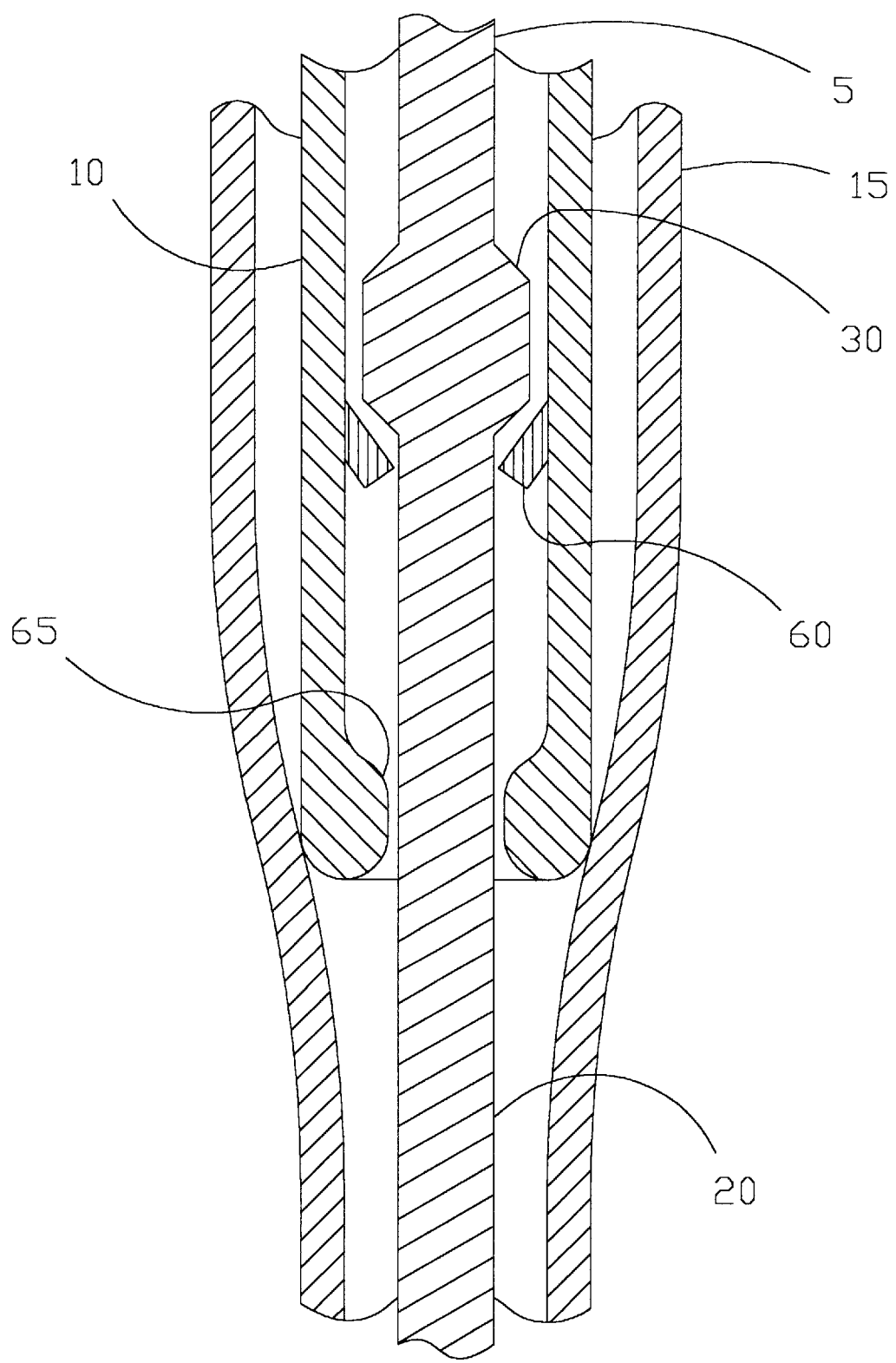
FIG. 2A is a sectional view of a portion of one embodiment of a distal protection introducer system in an unlatched condition.
Figure 2C:
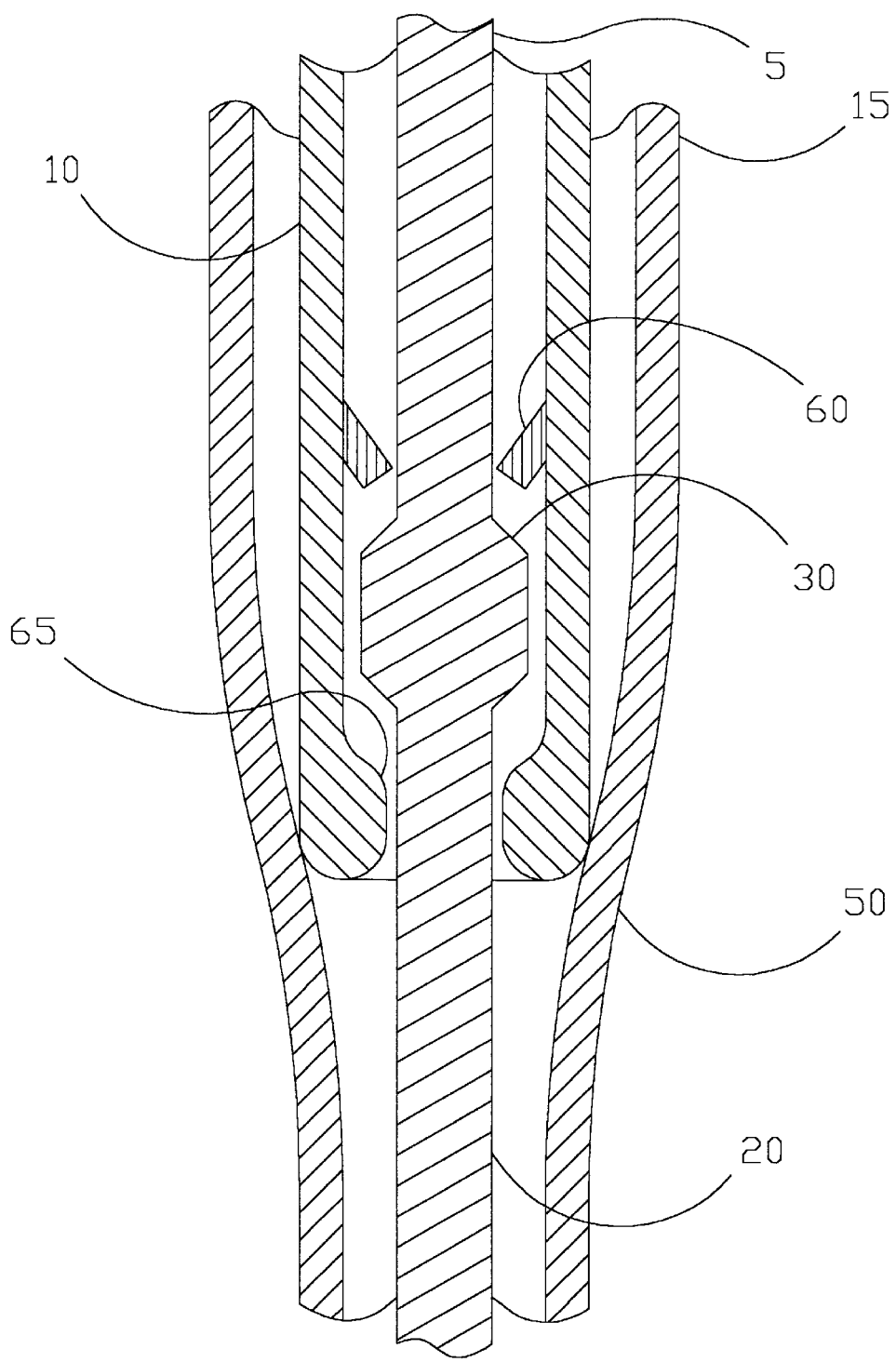
FIG. 2C is the sectional view of FIG. 2A in a latched condition.

FIGS. 2A–2C illustrate a portion of one embodiment of a distal protection system during various stages of deployment. In FIG. 2A the lockable guidewire (5) has been positioned percutaneously within the vasculature to an appropriate location with respect to the vascular lesion (not shown) and the distal introducer (15) containing the filter assembly (10) has been advance over the lockable guidewire (5) to a position where the ejector latch (60) is located proximal to the ferrule (30). Further advancement of the introducer with respect to the lockable guidewire (5) while maintaining the position of the lockable guidewire (5), or small withdrawal of the lockable guidewire (5) while maintaining the position of the distal introducer (15) causes the ejector latch (60) to move aside as shown in FIG. 2B and allow the ferrule (30) to pass proximal to the ejector latch (60) as shown in FIG. 2C.

Figure 3:
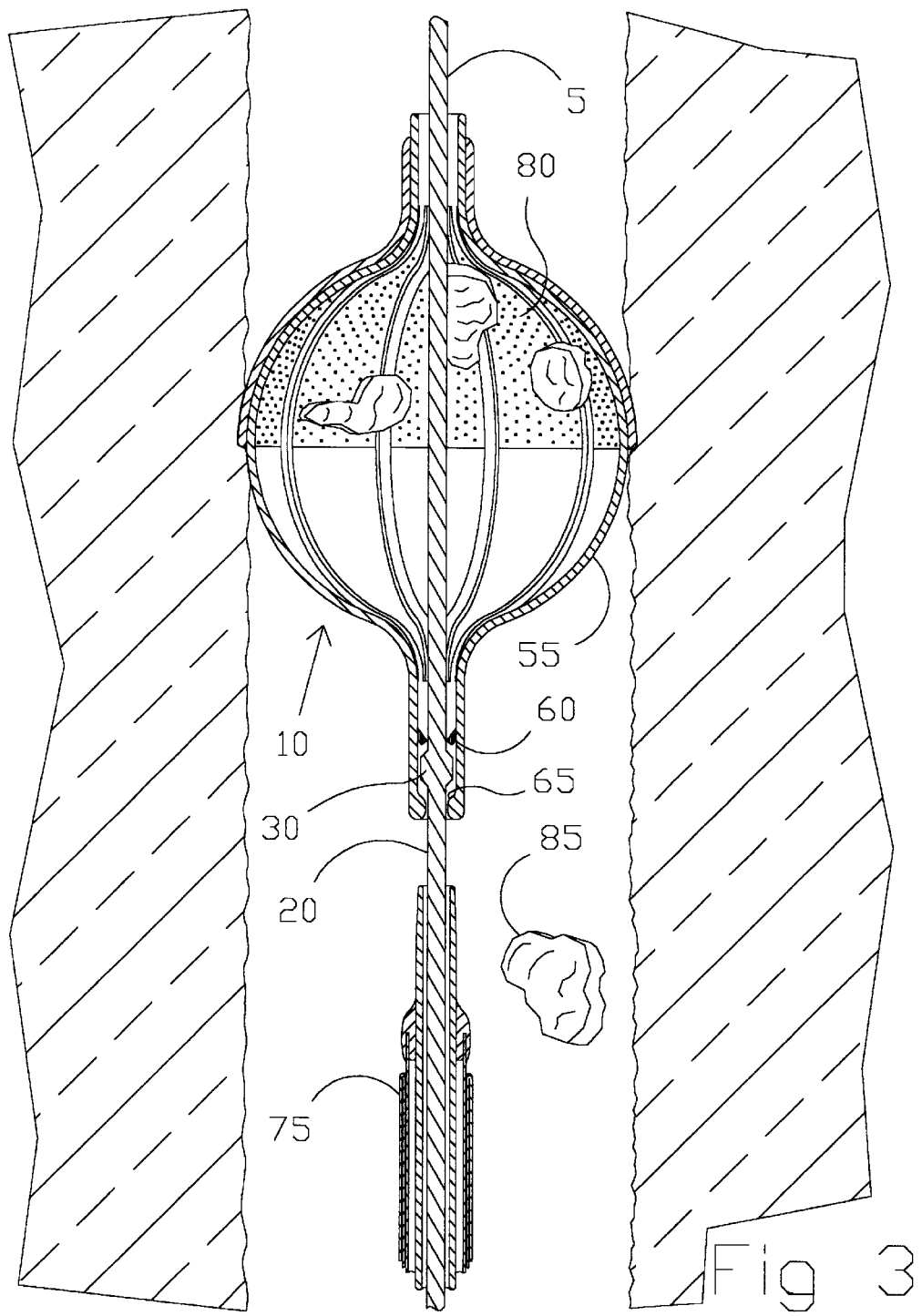
FIG. 3 is a sectional view of an embodiment of a distal protection and introducer system that remains latched in a deployed condition.

Withdrawal of the distal introducer (15) or advancement of the lockable guidewire (5) results in direct interface or contact of the ferrule (30) with the ejector latch (60) and ejection of the filter assembly (10) from the distal introducer (15) as shown in FIG. 3. The expanding support structure (55) has expanded out to an enlarged diameter or deployed state that is approximately the same size as the vessel that is being treated. In this embodiment the ejector latch (60) remains latched following deployment of the filter assembly (10) as the ejector latch (60) moves to a position to prevent passage of the ferrule (30) distally. The lockable guidewire (5) cannot be moved distally with respect to the filter assembly (10) due to interaction of the ferrule (30) with the ejector latch (60). Following removal of the distal introducer (15) from the lockable guidewire trunk (20), the lockable guidewire trunk (20) can now be used to provide a pathway for an angioplasty or other therapeutic or diagnostic catheter (75) to reach the site of the lesion. A porous filter material (80) is attached to the expanding support structure (55) to allow blood to flow through it from proximal to distal of the filter assembly (10) while capturing any emboli (85) that may have been generated during the angioplasty or other adjunctive therapeutic or diagnostic procedure. It may be desired to size the filter assembly (10) such that it is slightly larger than the vessel diameter to ensure a fit that will not allow emboli (85) to escape distal to the filter assembly (10). Following the completion of the angioplasty or other adjunctive therapeutic or diagnostic procedure, the introducer catheter (45) used to deliver the filter assembly (10) or an introducer catheter having approximately similar or larger diameter distal introducer (15) can be placed over the lockable guidewire trunk (20) and advanced to the location of the filter assembly (10) and the filter assembly (10) is withdrawn or partially withdrawn into the distal introducer (15). The lockable guidewire (5) along with the distal introducer (15) and filter assembly (10) containing embolic material are then withdrawn from the vasculature.

Figure 4:
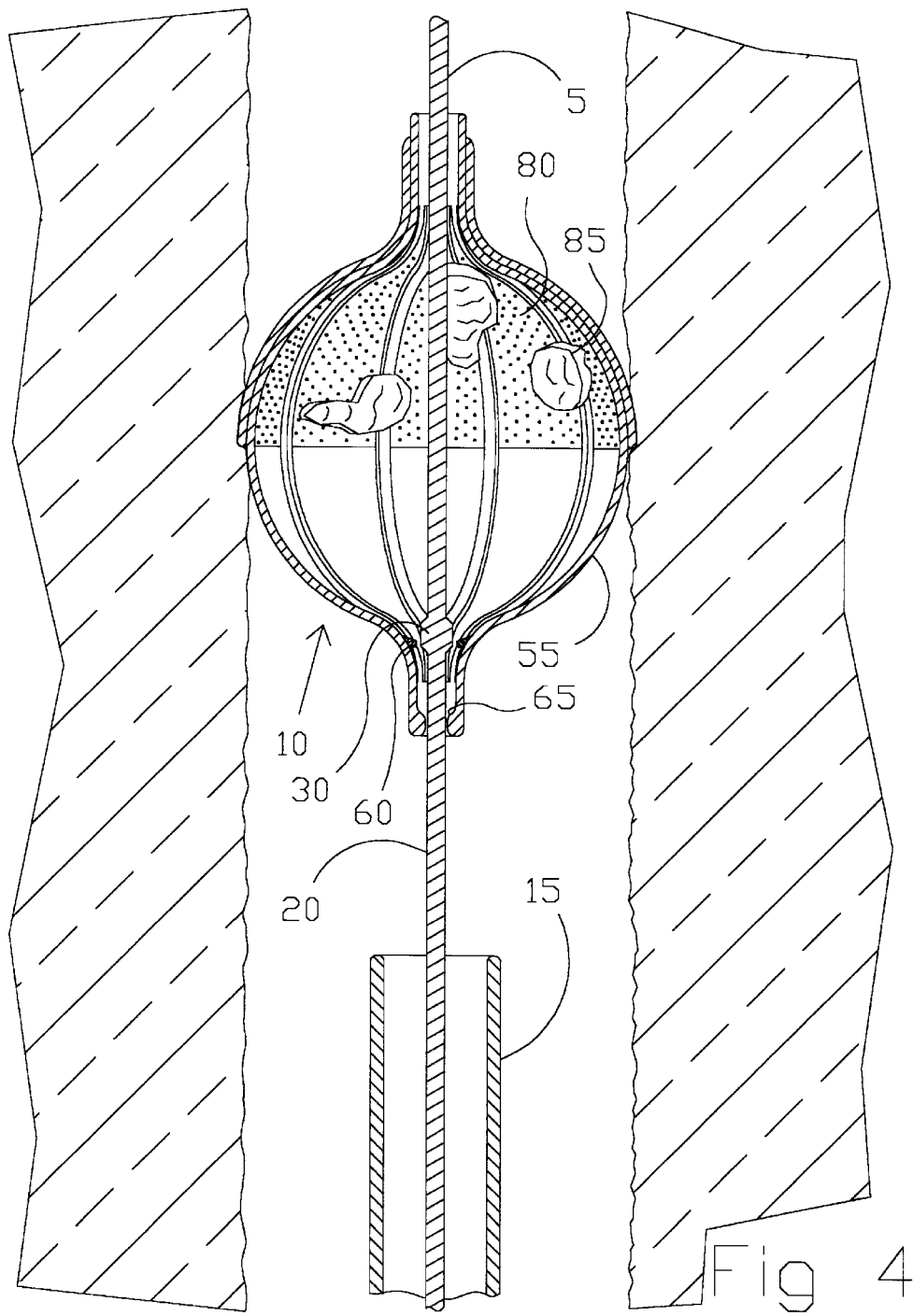
FIG. 4 is a sectional view of an embodiment of a distal protection and introducer system that unlatches in a deployed condition.

In an alternate embodiment the ejector latch (60) can unlatch following ejection of the filter assembly (10) from the distal introducer (15) as shown in FIG. 4. As shown in this illustration, the ejector latch (60) has moved outward along with the outward movement of the expanding support structure (55) releasing the ferrule (30) after the filter assembly (10) has been deployed. The release of the ejector latch (60) allows the lockable guidewire (5) and the ferrule (30) to be advanced further distally. The lockable guidewire (5) can then be repositioned distally if necessary to aid in adjunctive catheter placement. Additionally, slight movements of the lockable guidewire (5) during placement of other interventional catheters will not cause movement of the filter assembly (10) and possible trauma to the vessel.

Figure 5C:
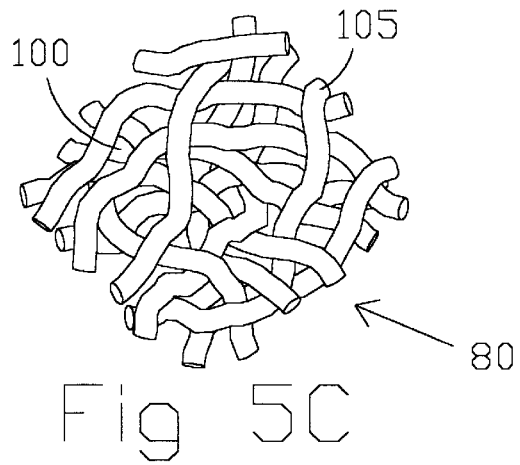
FIG. 5C is a plan view of a portion of a electrostatically spun polymeric material.
Figure 5B:
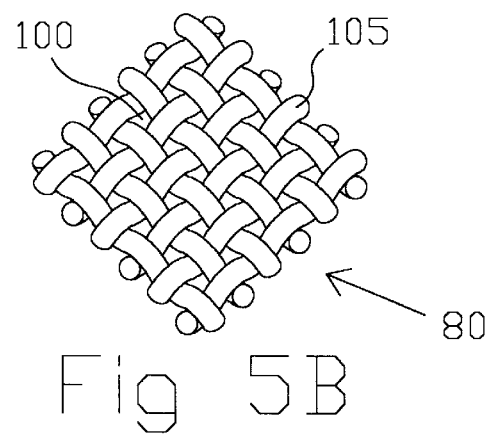
FIG. 5B is a plan view of a portion of a woven polymeric material.
Figure 5A:
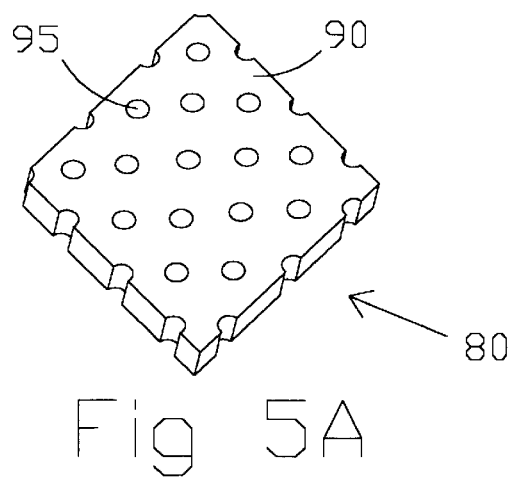
FIG. 5A is a plan view of a portion of a polymeric material containing holes.

FIGS. 5A–5C show examples of porous filter material (80) that can be used in the embodiments of this invention. It is understood that other porous filter materials can similarly be used with the present invention and that the present invention is not restricted to the filter materials described. FIG. 5A shows a polymeric material (90) through which holes (95) have been formed to allow blood flow to pass. The polymeric material (90) can be polyvinyl chloride, polyurethane, polyethyleneterephthalate, or other solution cast or thermally formed polymeric material or composite material. The holes (95) can be formed using mechanical means, ion beam, laser beam or other method to form holes (95) ranging in diameter from approximately 25–200 micrometers (0.001–0.008 inches). Holes (95) of this size will let blood cellular elements pass through yet will hold back embolic debris with diameter greater than the hole (95) size. The number of holes (95) is such that the blood flow through the filter assembly (10) is a significant percentage of the blood flow through the diseased vessel without the filter assembly (10) such that clinical sequelae do not arise.

FIG. 5B shows a porous filter material (80) formed of a woven, braided, knit, expanded polytetrafluoroethylene, expanded polypropylene, or other fibrous material used to form a thin porous material. The spacing between (100) fibers (105) or strands can be similar to the hole (95) diameters stated for the porous filter material (80) of FIG. 5A.

FIG. 5C shows a porous filter material (80) formed from a polymeric material (90) that is electrostatically spun, sprayed, or otherwise extruded onto a surface to form a thin porous material with the fibers (105) melted or joined together at crossover points through a solvent bond or a melt bond. Other techniques used to form expanded porous materials such as expanded polytetraflouroethylene material can also be used. The porous structure of such materials can be made to vary throughout the wall thickness there by forming a larger pore size prefilter followed by a smaller pore size final filter. The prefilter can have a pore size or spacing that can range from 100–500 micrometers. The final filter can have a pore size or spacing similar to that described earlier. The fiber (105) spacing (100) is similar to that of FIG. 5B.

FIGS. 6A–6C show an embodiment of the filter assembly (10) shown in FIG. 4. Shown in FIG. 6A is a filter assembly (10) in an undeployed condition within the distal introducer (15). The distal introducer (15) can have a tip region (110) that is more flexible than the rest of the distal introducer (15). The tip region (110) can aid in maneuvering the distal introducer (15) through the vasculature to the appropriate location. The expanding support structure (55) can be formed out on Nitinol or other elastic flat wires or wires with memory retention that are attached to a distal band (115). The distal band (115) is able to slide axially along the lockable guidewire (5) as the filter assembly (10) transforms from a smaller diameter in its undeployed state to a larger diameter in its deployed state as in FIG. 6B. The expanding support structure (55) is also attached to a proximal band (120). The proximal band (120) has a filter stop (65) that has clearance from the lockable guidewire trunk (20) but does not have clearance with the ferrule (30) so that the filter assembly (10) can at no time ever be released from off the distal end (35) of the lockable guidewire (5). The proximal (120) and distal (115) bands can be contiguous with the expanding support structure (55) and can be formed from a tube of metal that has been slotted using a variety of methods including laser, chemical etch, machining, and others. Alternately, the proximal (120) and distal (115) bands can be attached to a expanding support structure (55) formed of wire using an adhesive or metallic weld or braze. Upon deployment of the filter assembly (10) from the distal introducer (15), the ejector latch (60) is shown releasing the ferrule (30) to allow the lockable guidewire (5) to move distally with respect to the filter assembly (10). The porous filter material (80) is attached to the expanding support structure (55) and forms a cup-shaped emboli collector in its deployed state. A similar structure of the filter assembly (10) can have an ejector latch (60) that remains latched following deployment of the filter assembly (10) as described in FIG. 3.

FIG. 6C shows another embodiment of the filter assembly (10) shown in FIGS. 6A and 6B but without an ejector latch to deploy the filter assembly (10). Instead the introducer catheter (45) has an ejector tube (125) that is used to deploy the filter assembly (10). The ejector tube (125) serves as an ejector means to provide relative movement between the filter assembly and the distal introducer (15). This is done by ether holding the ejector tube (125) and retracting the introducer catheter (45) or holding the introducer catheter (45) and advancing the ejector tube (125). However both the filter assembly (10) from FIGS. 6A and 6C are withdrawn from the vasculature in the same way as described for FIG. 3.

Figure 7A:
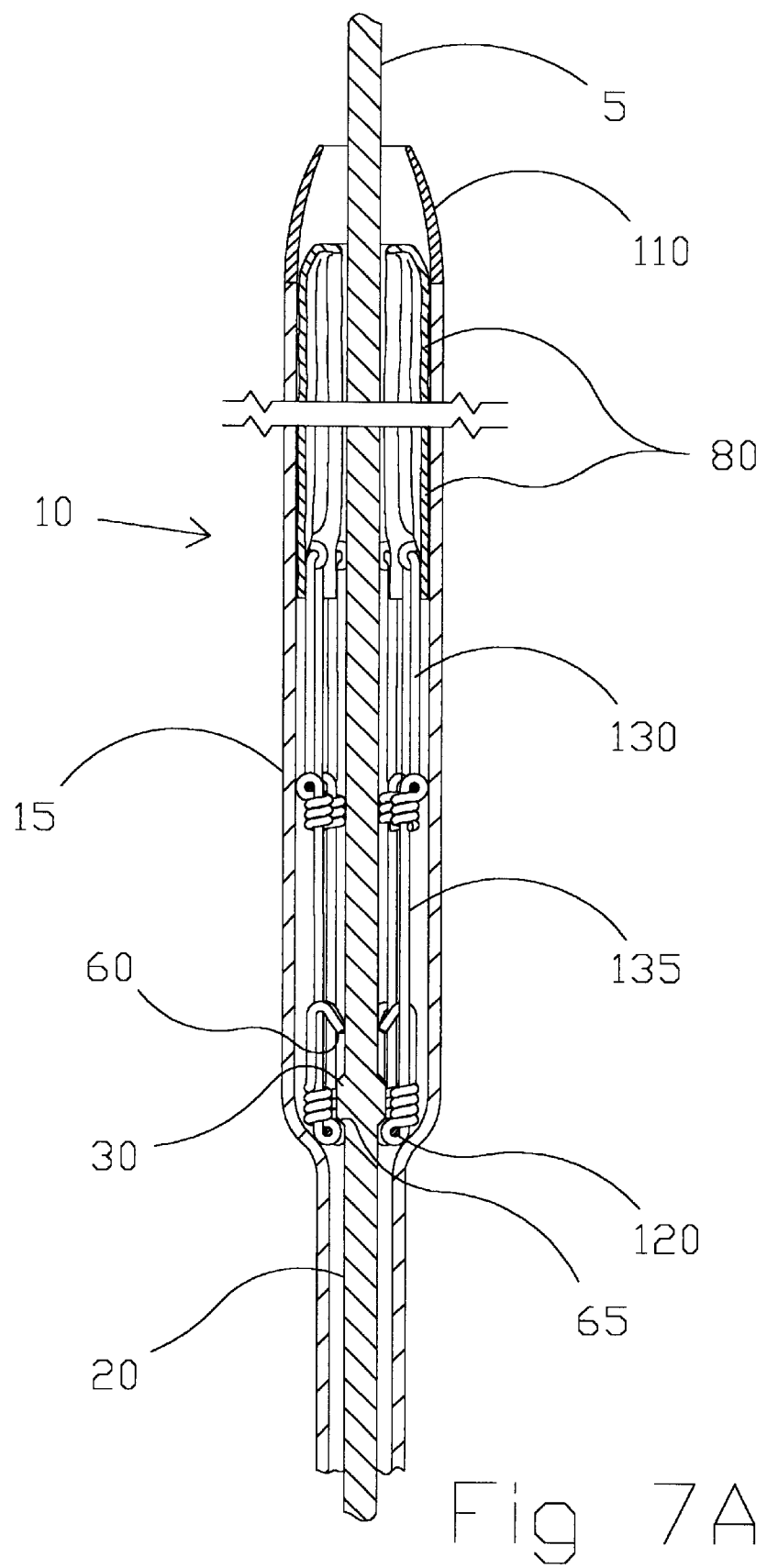
FIG. 7A is a detailed partially sectioned view of an alternate embodiment of a distal protection and introducer system in a latched but undeployed condition.
Figure 7C:
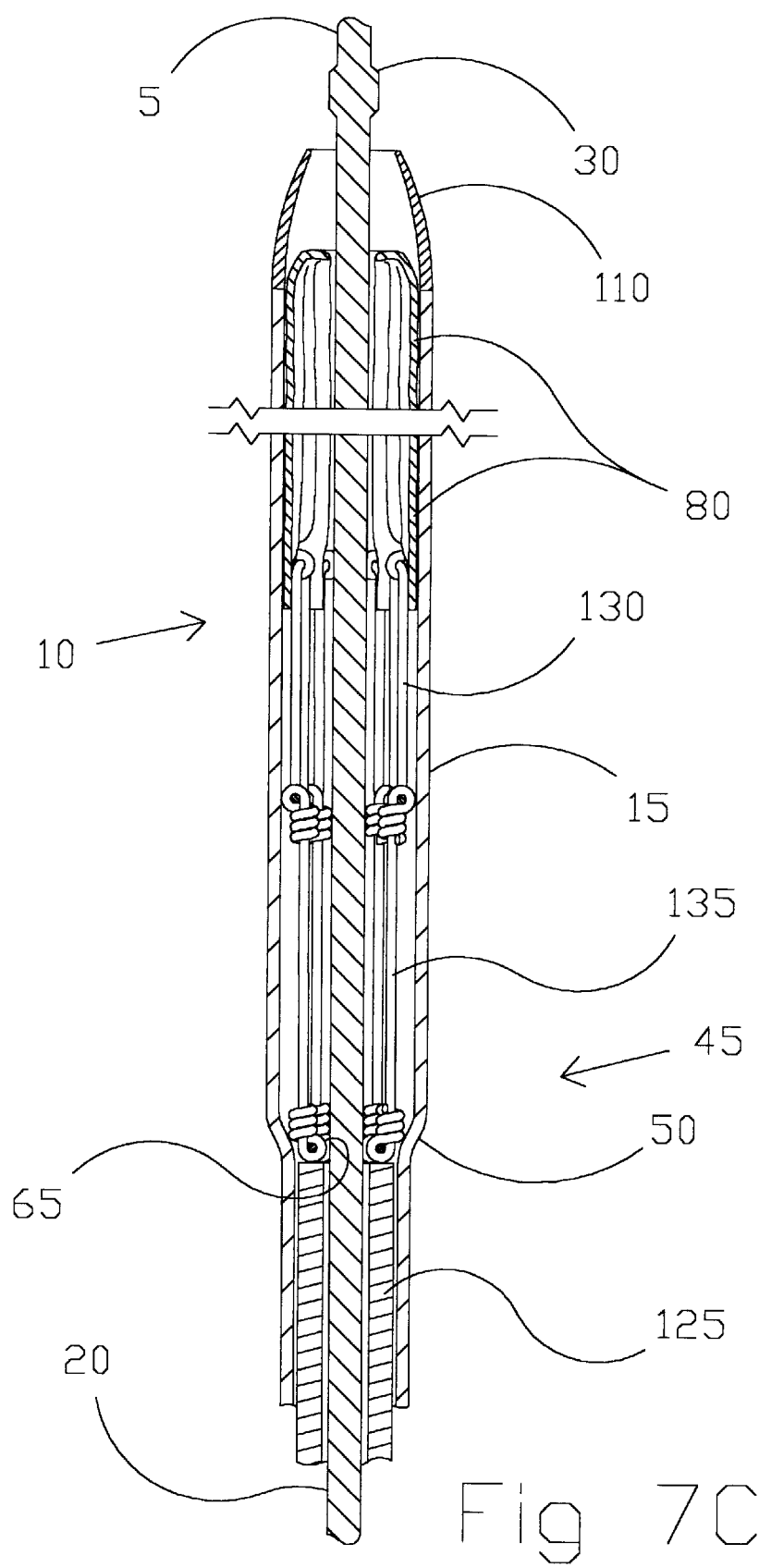
FIG. 7C is a detailed partially sectioned view of an embodiment similar to that of FIG. 7A in an undeployed condition but that uses an ejection tube to deploy.

FIGS. 7A–7C shows another alternate embodiment for a filter assembly (10) of FIG. 4. Shown in FIG. 7A is a filter assembly (10) in its undeployed state. The distal introducer

(15) can have a tip region (110) that is more flexible than the rest of the distal introducer (15). The tip region (110) can aid in maneuvering the distal introducer (15) through the vasculature to the appropriate location. A self-expanding zig zag stent-like structure forms an expanding ring member (130) that can expand from a smaller nondeployed diameter from within the distal introducer (15) to a larger diameter similar to that of the blood vessel. The expanding ring member (130) can be formed from Nitinol or other shape memory metal or elastic material. Proximal filter supports (135) attach the expanding ring member(120) to a proximal band (120) which has clearance from the lockable guidewire trunk (20). An ejector latch (60) provides interface with the ferrule (30) of the lockable guidewire (5) during ejection of the filter assembly (10) from the distal introducer (15).

FIG. 7B shows the filter assembly (10) in a deployed state. A porous filter material (80) is attached to and is distal to the expanding ring member (130). The porous filter material (80) forms a cup-shaped emboli collector that prevents emboli from escaping distally from the filter assembly (10) yet allowing blood flow to pass through with non clinically significant flow reduction. Also as shown in FIG. 7B, the ejector latch (60) has moved outward along with the outward movement of the Proximal filter supports (135) releasing the ferrule (30) after the filter assembly (10) has been deployed. The release of the ejector latch (60) allows the lockable guidewire (5) and the ferrule (30) to be advanced further distally. The lockable guidewire (5) can then be repositioned distally if necessary to aid in adjunctive catheter placement. For example, placement of a stiffer more proximal portion of the lockable guidewire (5) into a more distal position within the blood vessel may help with the delivery of other interventional catheters to the lesion site. Additionally, slight movements of the lockable guidewire (5) during placement of other interventional catheters will not cause movement of the filter assembly (10) and possible trauma to the vessel. The filter stop (65) provides interface with the ferrule (30) to provide relative movement of the filter assembly (10) with respect to the distal introducer (15) during removal of the filter assembly (10) following completion of the therapeutic or diagnostic treatment.

FIG. 7C shows another embodiment of the filter assembly (10) shown in FIGS. 7A and 7B but without an ejector latch to deploy the filter assembly (10). Instead the introducer catheter (45) has an ejector tube (125) that is used to deploy the filter assembly (10). This is done by ether holding the ejector tube (125) and retracting the introducer catheter (45) or holding the introducer catheter (45) and advancing the ejector tube (125). However both the filter assemblies (10) from FIGS. 7A and 7C are withdrawn from the vasculature in the same way as described for FIG.3.

Figure 8A:
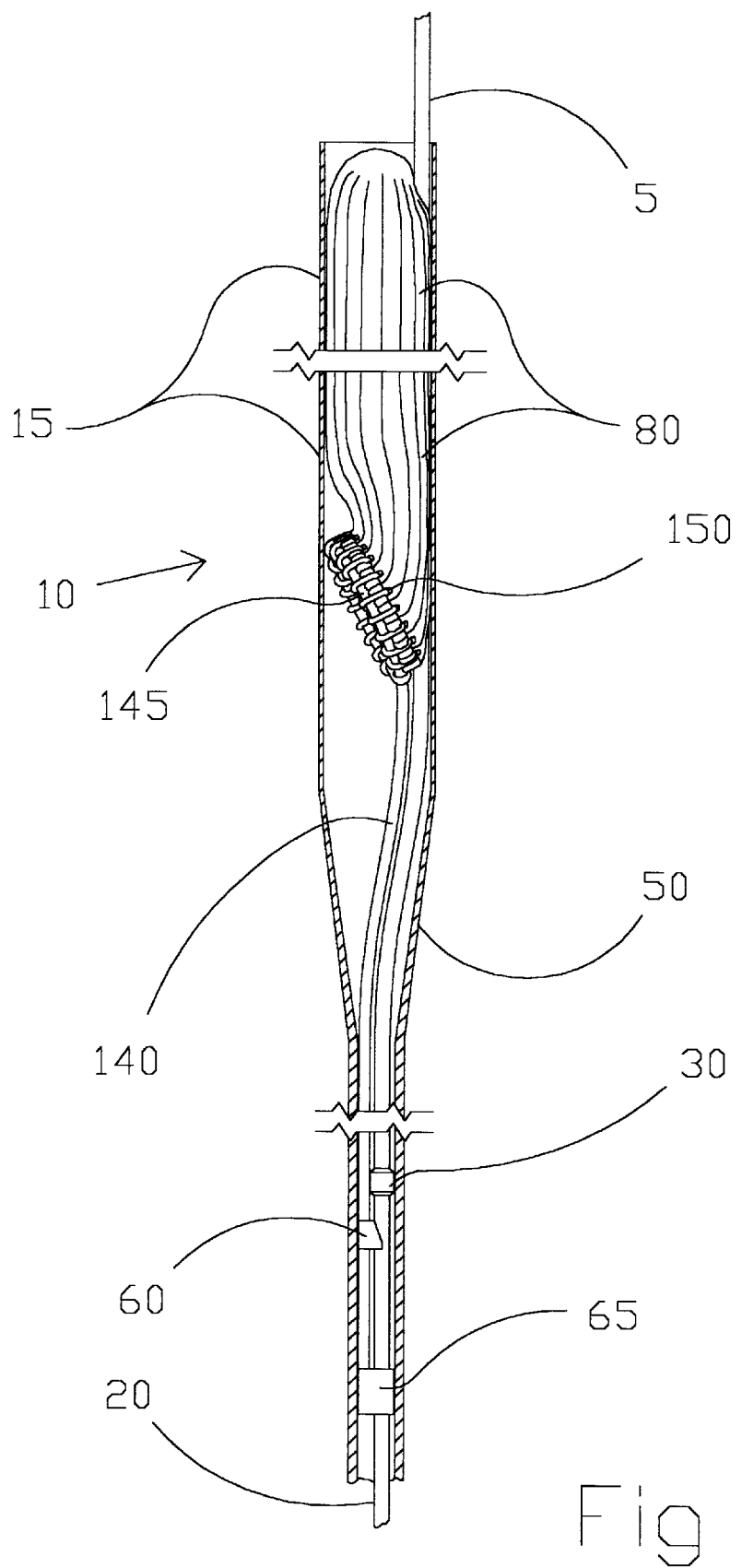
FIG. 8A is a detailed partially sectioned view of an alternate embodiment of a distal protection and introducer system in an unlatched and undeployed condition.
Figure 8D:
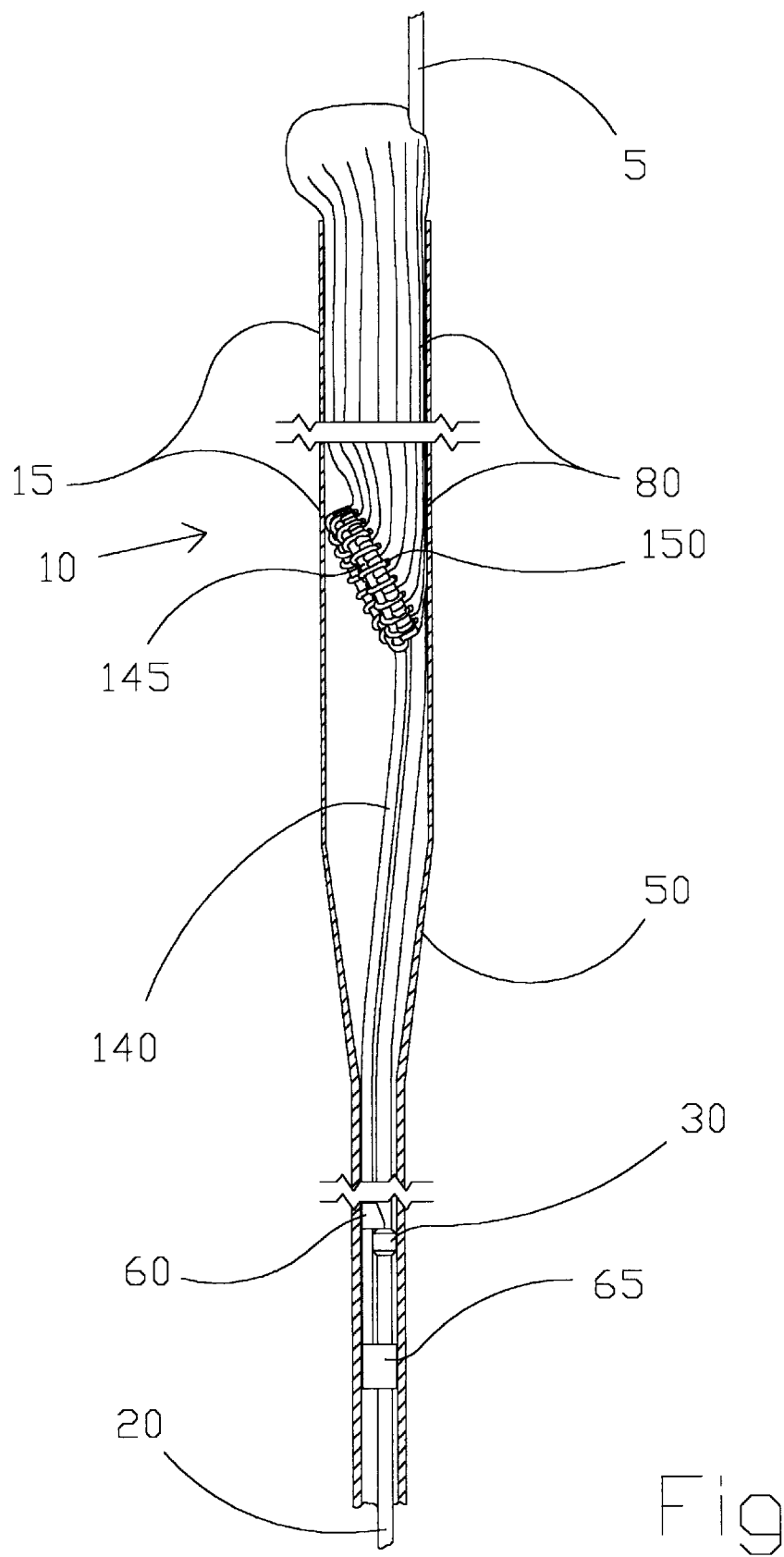
FIG. 8D is the detailed partially sectioned view of FIG. 8A in the process of ejecting.

FIGS. 8A–8F show yet another embodiment of the distal protection system of the present invention. The lockable guidewire (5) has a ferrule (30) located on it similarly to the lockable guidewire (5) shown in FIG. 1A. The distal introducer (15) has an introducer step (50) to hold the filter assembly (10) from moving proximally with respect to the distal introducer (15) during insertion of the distal introducer (15) containing the filter assembly (10) over the lockable guidewire (5). The filter assembly (10) has a filter stop (65) attached to one end of an elastic wire (140) such as a Nitinol wire; the lockable guidewire trunk (20) can pass axially through the filter stop (65), but the ferrule (30) is not able to pass through. The filter assembly (10) has a beveled ejector latch (60) attached to the elastic wire (140). In the distal introducer (15) the elastic wire (140) forms an expanding loop (145). Joining sites (150) are located along the expanding loop (145) and serve as attachment sites for the porous filter material (80) which can have a structure similar to that described earlier in FIGS. 5A–5C. During insertion into the vasculature the lockable guidewire (5) is first inserted and delivered to the site of the lesion. The introducer containing the filter assembly (10) is then advanced over the lockable guidewire (5) with the lockable guidewire trunk (20) passing through the filter stop (65) and the distal introducer (15) step (50) providing direct interaction with the filter assembly (10) (see FIG. 8A) to push it distally to the site of the vascular lesion. As the distal introducer (15) is further advanced with respect to the lockable guidewire (5) the bevel ejector latch (60) passes adjacent to the ferrule (30) as shown in FIG. 8B and the ferrule (30) is then located between the bevel ejector latch (60) and the filter stop (65) as shown in FIG. 8C. The distal introducer (15) can then be withdrawn proximally while maintaining the lockable guidewire (5) in a fixed position or the lockable guidewire (5) can be advanced while maintaining the distal introducer (15) in a fixed position to begin moving the filter assembly (10) distally within the introducer as shown in FIG. 8D. The beveled ejector latch is functioning as an ejector as it interacts with the ferrule (30) during ejection of the filter assembly (10) from the distal introducer (15).

Figure 8E:
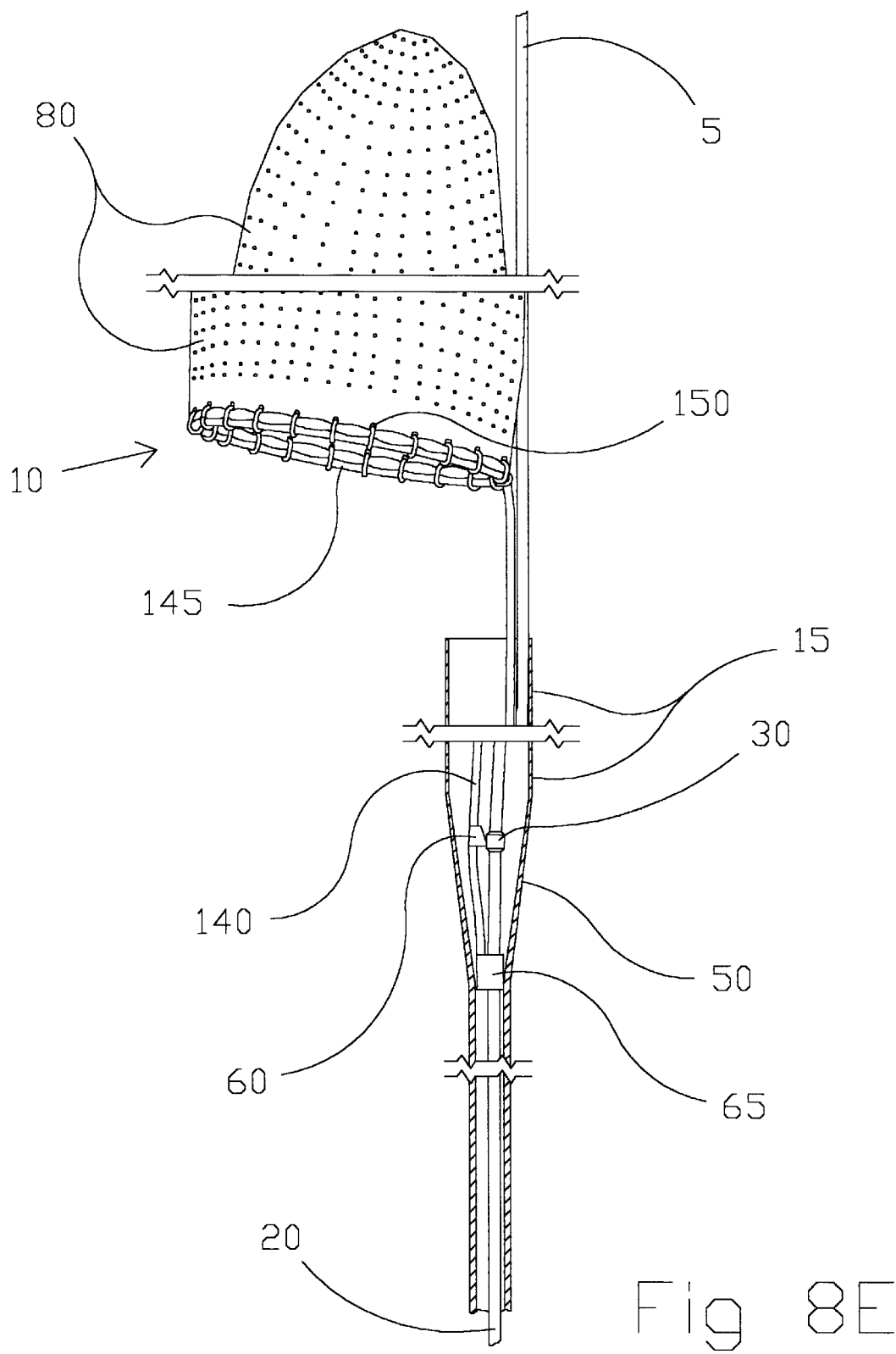
FIG. 8E is the detailed partially sectioned view of FIG. 8A in a deployed condition in the process of unlatching.
Figure 8F:
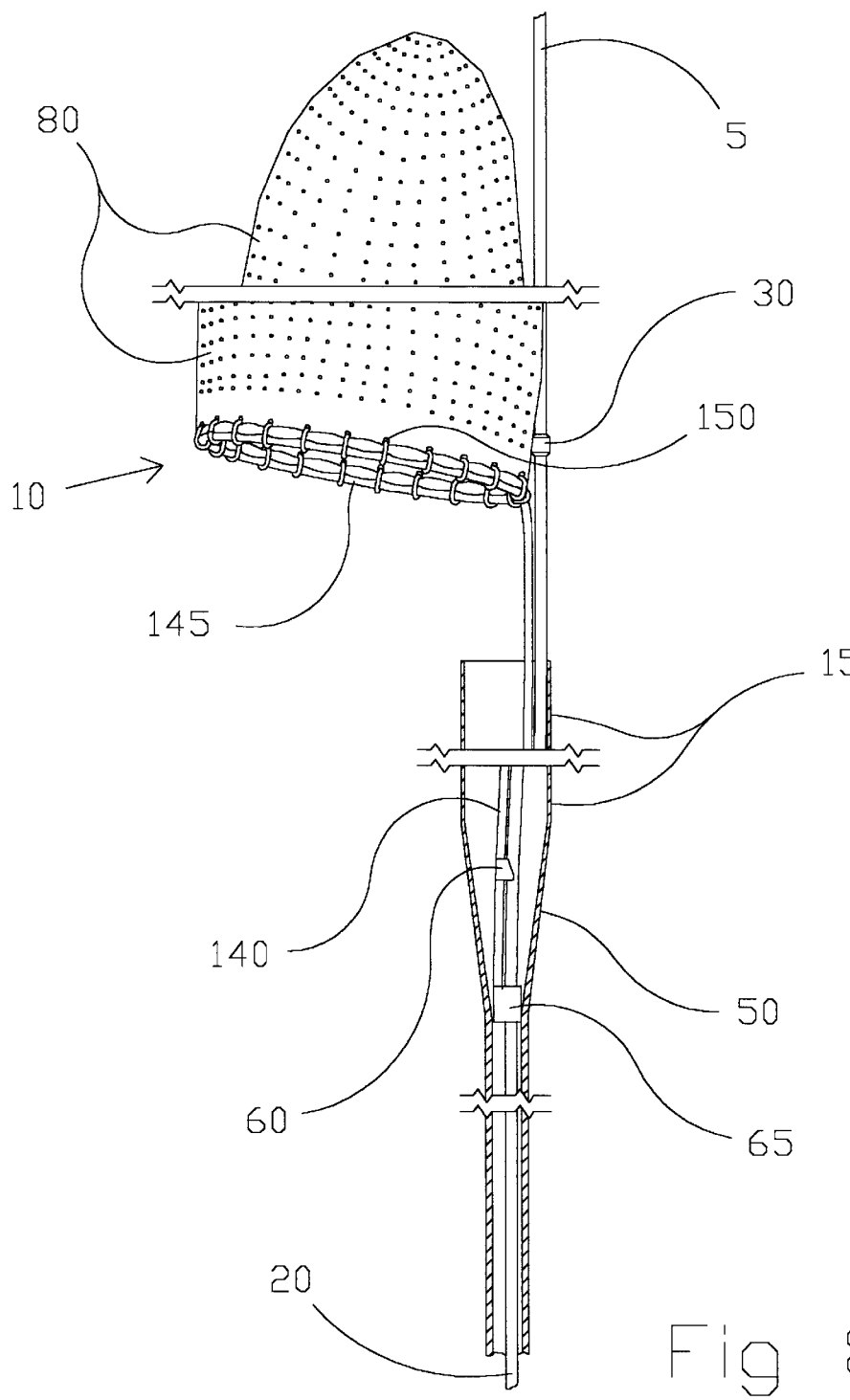
FIG. 8F is the detailed partially sectioned view of FIG. 8E in an unlatched condition.

FIG. 8E shows the filter assembly (10) shown in FIGS. 8A–8D following ejection from the distal introducer (15) with the expanding loop (145) enlarging to a larger diameter similar to the diameter of the vessel being treated. The expanding loop (145) member has enlarged in a manner similar to a lasso with the elastic wire (140) being fed through the feed hole (155). The amount of elastic wire (140) fed through the feed hole (155) can vary depending upon the diameter and perimeter of the blood vessel. This embodiment allows the expanding loop (145) to fit snugly within a large or small blood vessel depending upon The amount of elastic wire (140) that is fed through the feed hole (155) while expanding the loop as it enlarges to fit the blood vessel. The beveled ejector latch (60) is able to pass distally to the ferrule (30) once the ferrule (30) and bevel ejector latch (60) have been advanced far enough distally into the distal introducer (15) to provide space for the ferrule (30) to pass. This allows the lockable guidewire (5) to be advanced distally as shown in FIG. 8F without affecting the position of the filter assembly (10) in the vasculature. Additionally small movements of the lockable guidewire (5) which can occur during positioning of adjunctive catheters over the lockable guidewire (5) will not result in unwanted movement of the filter assembly (10) resulting in possible trauma to the vessel. The distal introducer (15) can be removed from the lockable guidewire (5) by pulling the introducer catheter (45) proximally and an angioplasty or other interventional catheter can be placed over the lockable guidewire (5) and delivered to the site of the lesion with the filter assembly (10) in place distal to the lesion in order to collect embolic debris. Following the interventional procedure, the interventional catheter is removed. The introducer catheter (45) with the distal introducer (15) is then placed over the lockable guidewire (5) and advanced to the location of the filter assembly (10). The filter assembly (10) is then pulled into the distal introducer (15) as the ferrule (30) interfaces with the filter stop (65) of the filter assembly (10) and are withdrawn from the vasculature.

Figure 9A:
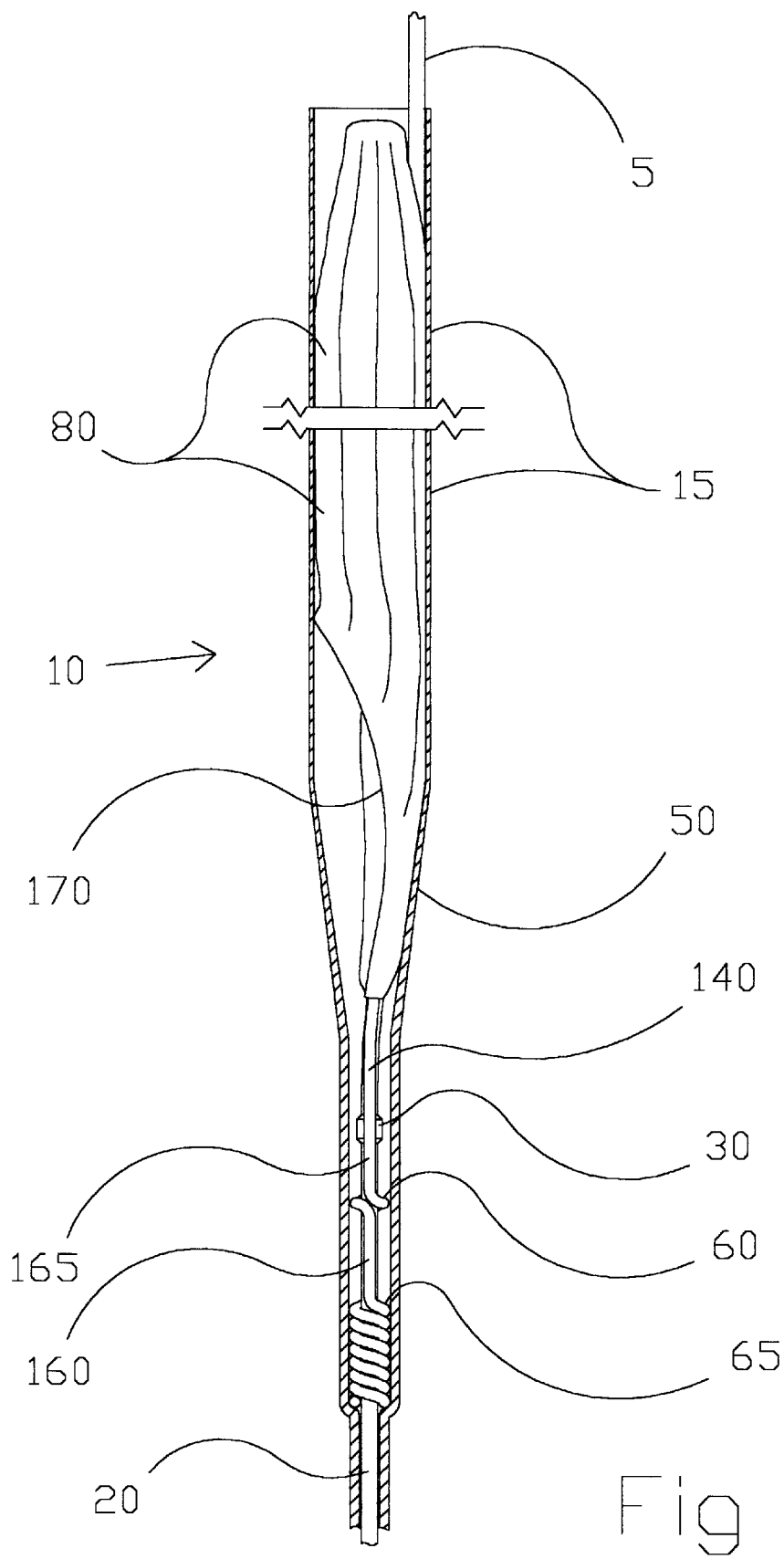
FIG. 9A is a detailed partially sectioned view of an alternate embodiment of a distal protection and introducer system in an unlatched and undeployed condition.
Figure 9B:
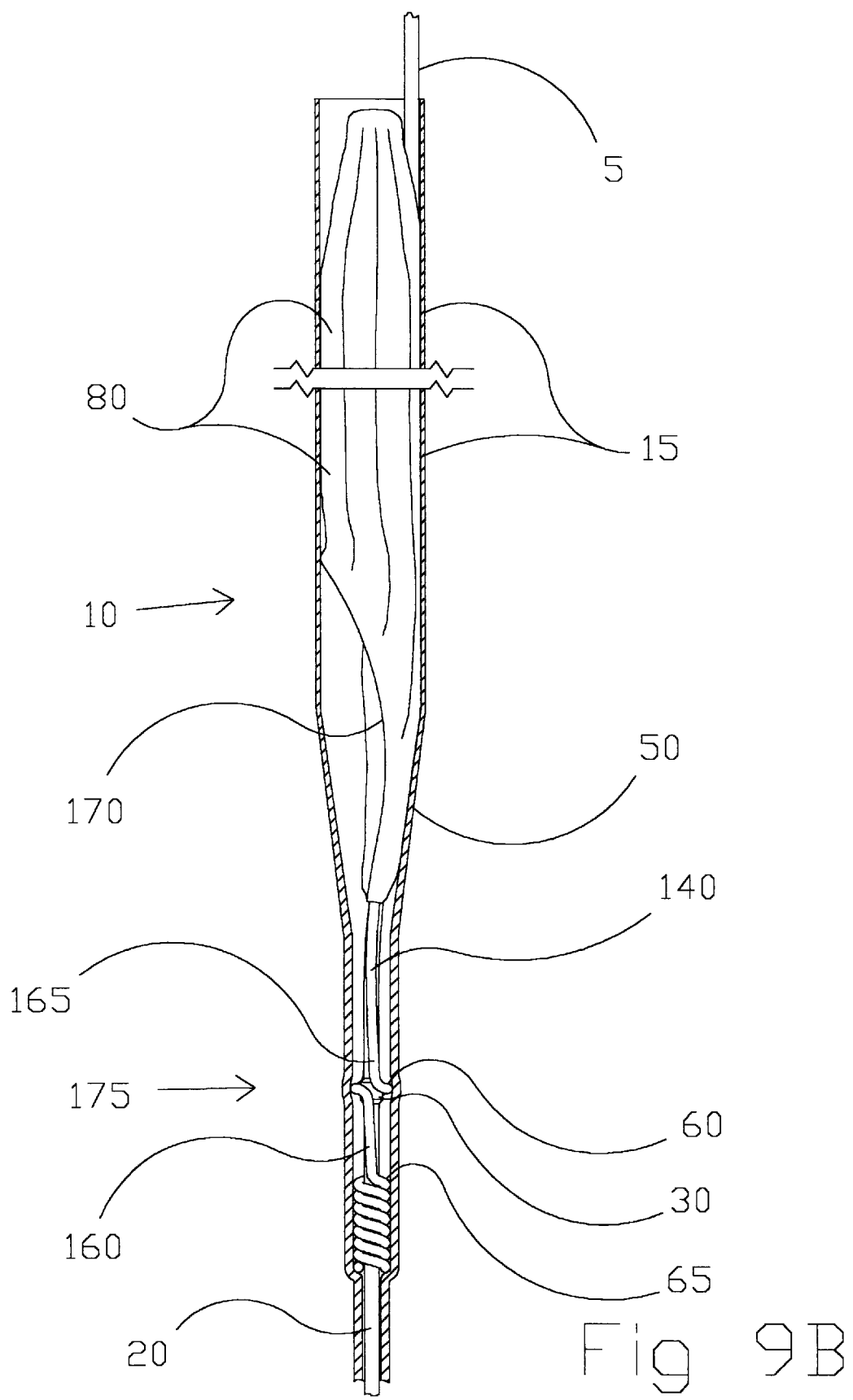
FIG. 9B is the detailed partially sectioned view of FIG. 9A in the process of latching.
Figure 9C:
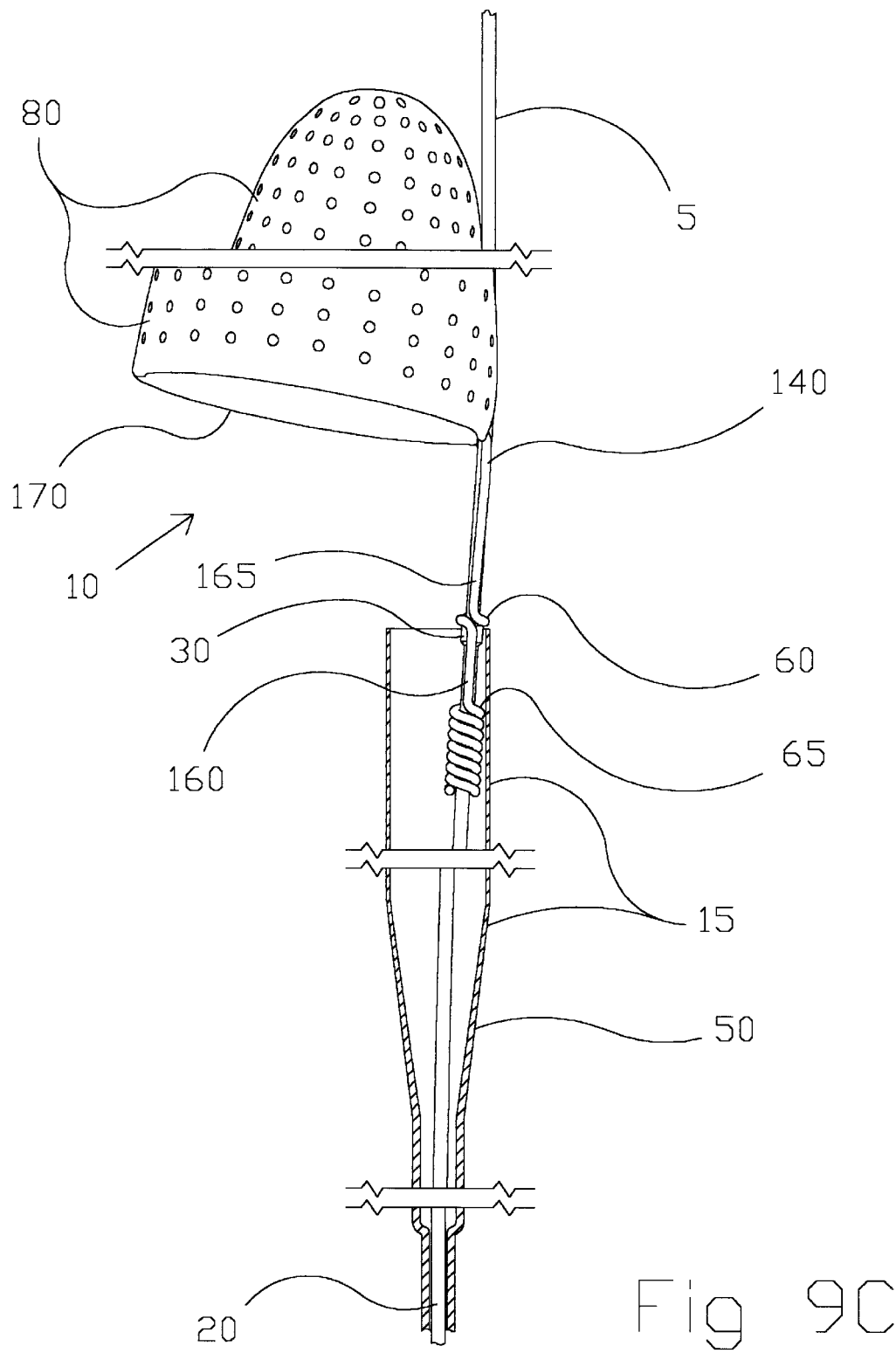
FIG. 9C is the detailed partially sectioned view of FIG. 9A in a deployed condition.

FIGS. 9A–9C show another embodiment of the distal protection system of the present invention with some changes made to the filter assembly (10). FIG. 9A shows a distal introducer (15) and a lockable guidewire (5) with similar features and reference numerals to the corresponding components of FIGS. 8A–8F. The filter assembly (10) of FIG. 9A is shown in a nondeployed condition. In this embodiment double elastic wires (140) such as Nitinol wires that are wound in a double helix to form the filter stop (65) and then have a short proximal straight region (160) extending distally a short distance to where it then forms an ejector latch (60). The elastic wires (140) continue on from the ejector latch (60) with a distal straight region (165) Farther distally within the distal introducer (15) to then form a constant length loop (170). The porous filter material (80) is attached to the constant length loop (170) by adhesive or during the forming process used to make the filter material.

FIG. 9B illustrates the ejector latch (60) made from the two elastic wires (140) separating as the ferrule (30) passes between them. Because of the short proximal straight region (160) length the force required to cause the ejector latch (60) to spread apart is higher than the force required to cause the filter assembly (10) move inside the distal introducer (15). The distal introducer (15) step (50) acts to hold the filter assembly (10) from moving proximally as the ferrule (30) located on the lockable guidewire (5) is being retracted with respect to the ejector latch (60)

FIG. 9C shows the filter assembly (10) being ejected out of the distal introducer (15) and into the blood vessel either through distal advancement of the lockable guidewire (5) or through proximal retraction of the distal introducer (15). The double elastic wires (140) are each fed out of the distal introducer (15) with each elastic wire (140) adding to a portion of a loop configuration or constant length loop (170). This constant length loop (170) will provide a seal with a large blood vessel with about the same perimeter as itself. Alternately, the constant length loop (170) can form an oblique angle with respect to a small blood vessel with a significantly smaller perimeter and form a seal with respect to it also. The porous filter material (80) is released into the blood vessel forming a wind-sock or cup-shaped emboli collection filter. In this embodiment the ferrule (30) of the lockable guidewire (5) is locked between the ejector latch (60) and the filter stop (65) of the filter assembly (10). Movement of the lockable guidewire (5) can result in the transfer of some force or movement of the filter assembly (10). The filter assembly (10) can be retracted back into the distal introducer (15) following completion of all adjunctive therapeutic or diagnostic procedures by pulling proximally on the lockable guidewire (5).

Figure 9D:
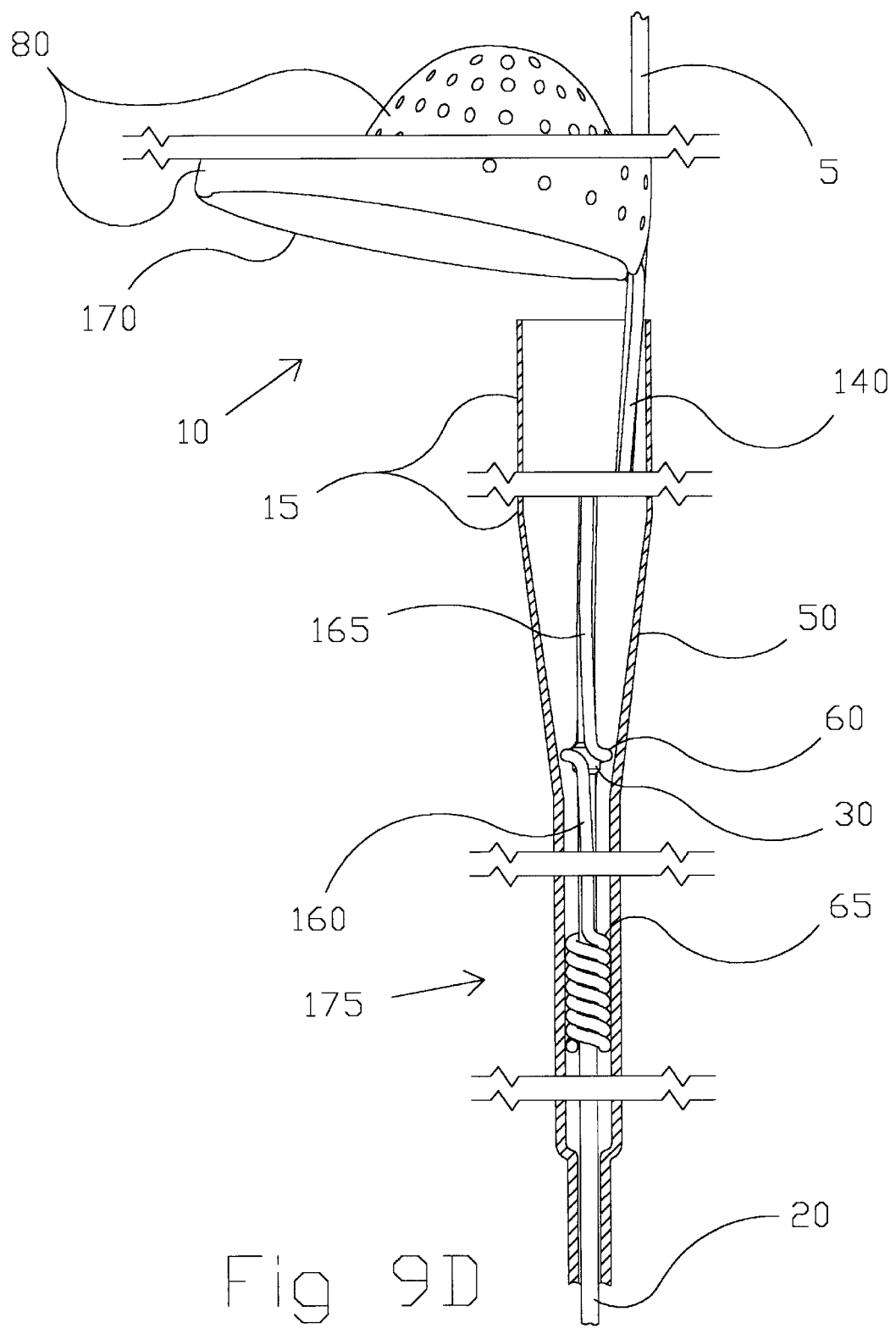
FIG. 9D is a detailed partially sectioned view of an embodiment similar to that of FIG. 9A in the process of unlatching.

FIG. 9D Shows one more embodiment of the filter assembly (10) having a proximal straight region (160) and a distal straight region (165) that is longer in length than the similar components shown in FIG. 9C. After deployment of the filter assembly (10) from the distal introducer (15) the increased length of the proximal straight region (160) allows the ejector latch (60) region to spread apart with a very small applied force making it possible for the ferrule (30) to move distal with respect to the ejector latch (60). The lockable guidewire (5) can then be repositioned distally if necessary to aid in adjunctive catheter placement. For example, placement of a stiffer more proximal portion of the lockable guidewire (5) into a more distal position within the blood vessel may help with the delivery of other interventional catheters to the lesion site. Additionally, slight movements of the lockable guidewire (5) during placement of other interventional catheters will not cause movement of the filter assembly (10) and possible trauma to the vessel. To provide the ejector latch (60) region with the ability to resist spreading during deployment, the introducer catheter (45) is made to have a latch constraint region (175). The latch constraint region (175) prevents the ejector latch (60) from spreading so that the force required to cause the ejector latch (60) to spread apart will be greater than the force required to cause the filter assembly (10) to move while inside the distal introducer (15).

Figure 9E:
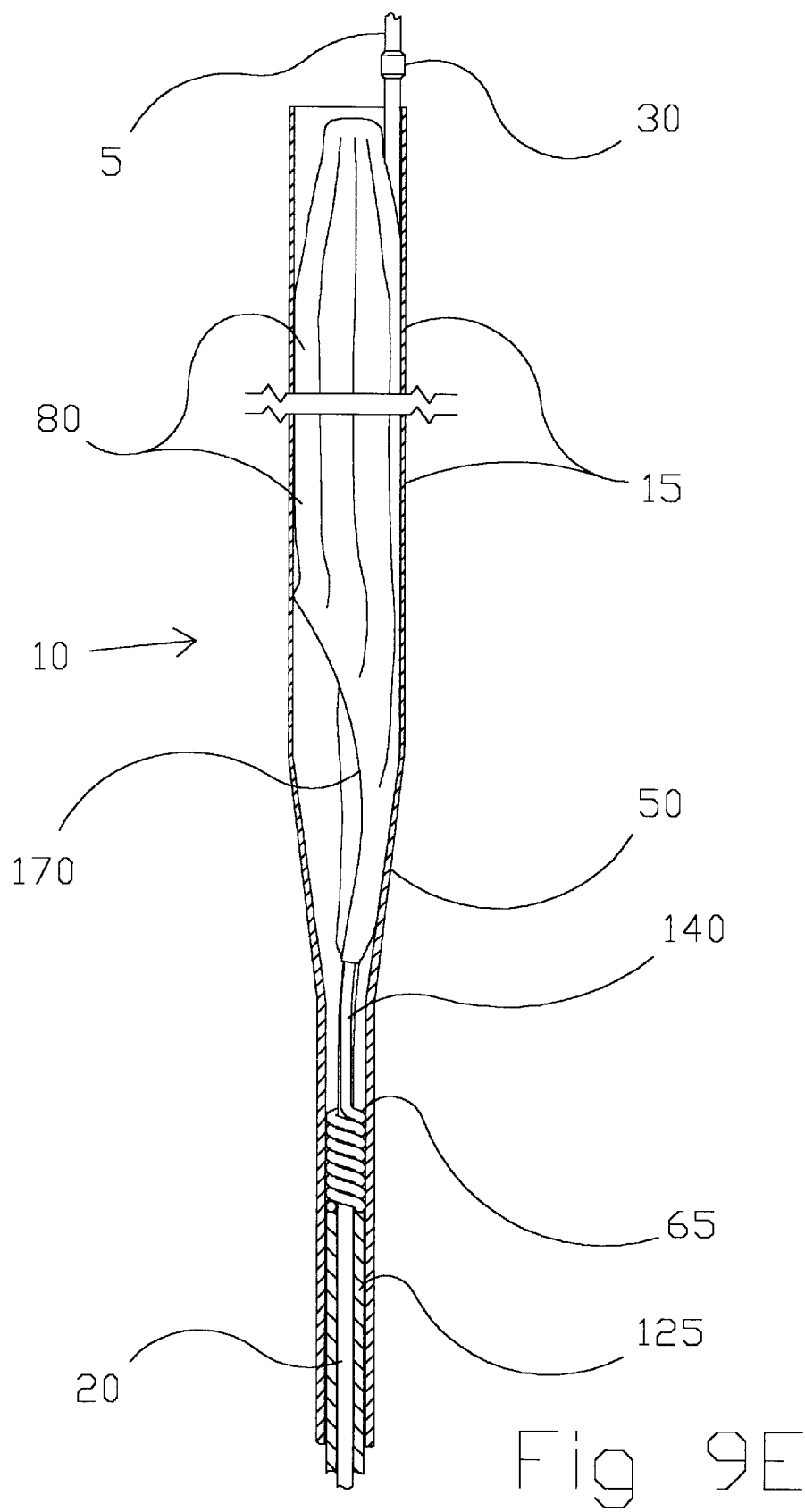
FIG. 9E is a detailed partially sectioned view of an embodiment similar to that of FIG. 9A in an undeployed condition but that uses an ejection tube to deploy.

FIG. 9E shows another embodiment of the filter assembly (10) shown in FIG. 9A but without an ejector latch to deploy the filter assembly (10). Instead the introducer catheter (45) has an ejector tube (125) that is used to deploy the filter assembly (10). This is done by ether holding the ejector tube (125) and retracting the introducer catheter (45) or holding the introducer catheter (45) and advancing the ejector tube (125). However both the filter assemblies (10) from FIGS. 9A and 9E are withdrawn from the vasculature in the same way as described for FIG.3.

Figure 10:
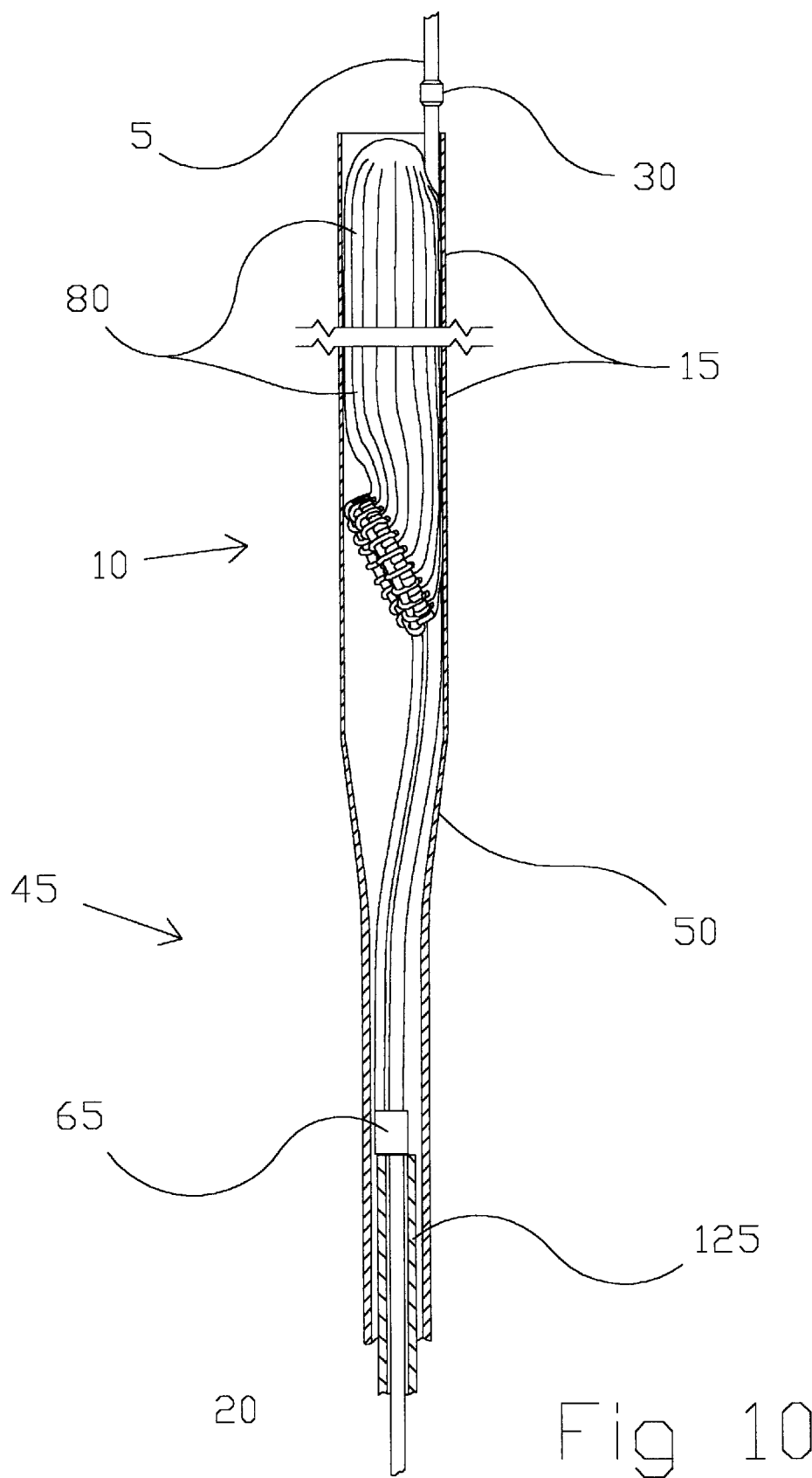
FIG. 10 is a detailed partially sectioned view of an embodiment similar to that of FIG. 8A in an undeployed condition but that uses an ejection tube to deploy.

Still yet another embodiment of the present invention is shown in FIG. 10 with the filter assembly (10) similar to that shown in FIGS. 8A–8F in a nondeployed condition. The introducer catheter (45) can have a generally cylindrical lumen throughout its entire length to provide passage for the filter assembly (10). The lockable guidewire (5) has a ferrule (30) which is similar to the ferrule (30) described in the previous embodiments. The filter assembly (10) has a filter stop (65) which serves as an interface with the ferrule (30) to pull the filter assembly (10) back into the distal introducer (15) following the therapeutic or diagnostic procedure. The filter assembly (10) of this embodiment is not required to have an ejector latch (60) as described in the previous embodiments. The filter assembly (10) is ejected from the distal introducer (15) with an ejector tube. (125) In normal use the lockable guidewire (5) is first advanced to the site of the lesion. The introducer catheter (45) containing the filter assembly (10) and the ejector tube (125) is advanced over the lockable guidewire trunk (20) until the filter assembly (10) is positioned within the blood vessel distal to the site of the lesion. The introducer catheter (45) is then retracted while maintaining the position of the ejector tube (125). Alternately, the filter assembly (10) can be ejected by holding the introducer catheter (45) steady while advancing the ejector tube (125) distally. Following ejection of the filter assembly (10) the introducer catheter (45) and ejector tube (125) can be removed by pulling them proximally with respect to the lockable guidewire trunk (20). The lockable guidewire (5) can then be advanced distally further within the blood vessel if desired. Additional angioplasty or other therapeutic or diagnostic catheters can then be advanced over the lockable guidewire trunk (20) in order to treat the vessel. Following vessel treatment these interventional catheters can be removed and the introducer catheter (45) can be advanced over the lockable guidewire trunk (20). The filter assembly (10) can be retracted along with its collected embolic debris either completely or partially into the distal introducer (15) by pulling proximally on the lockable guidewire (5) while maintaining the position of the introducer catheter (45).

Figure 11:
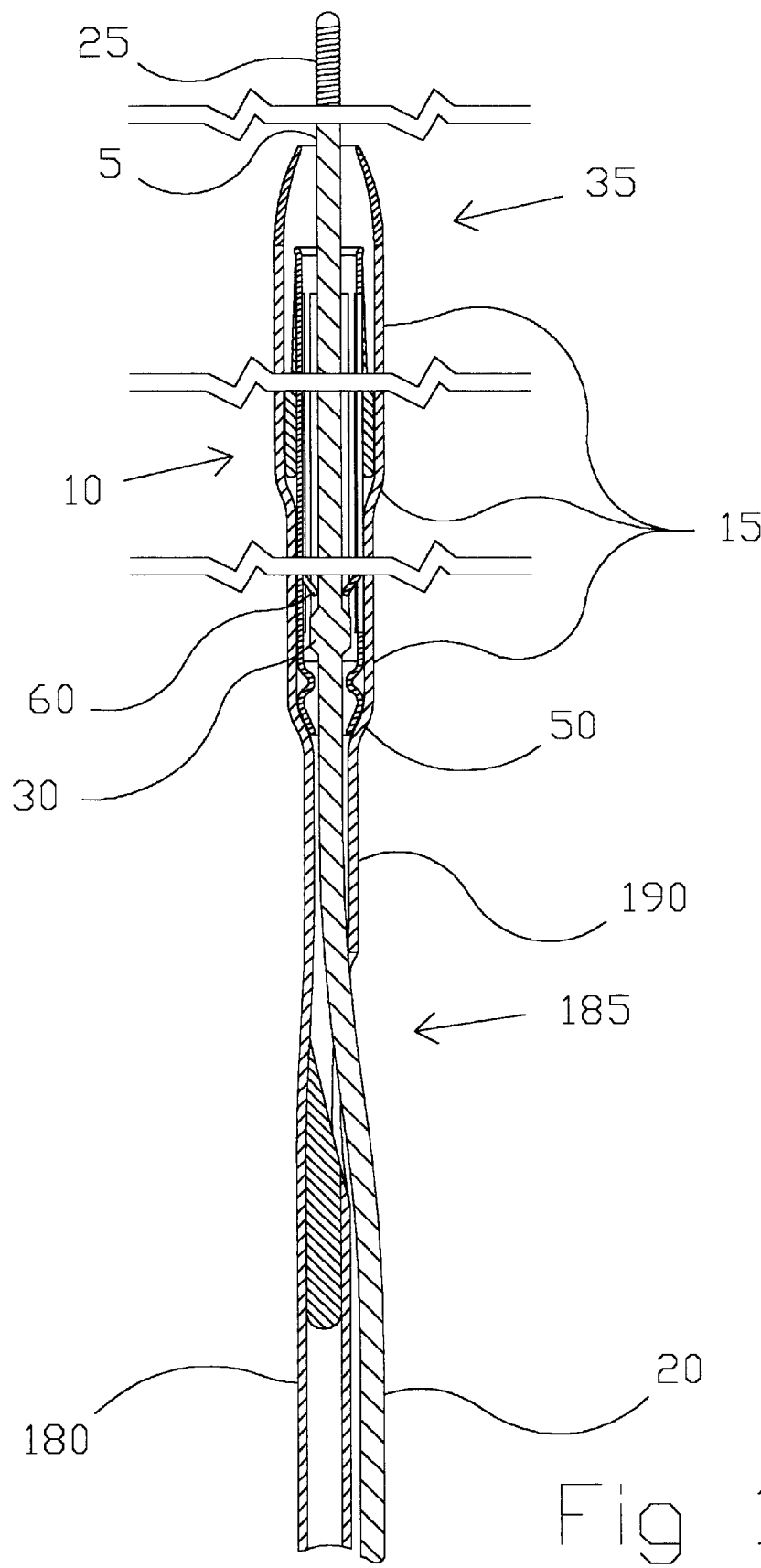
FIG. 11 is a detailed sectional view of an alternate embodiment of a distal protection and introducer system that has a rapid exchange configuration.

Due to the difficulty associated with working with extremely long exchange length guidewires which typically are about 300 cm long, it is sometimes advantageous to work with rapid exchange catheters that can be used with standard length guidewires of about 150 to 240 cm length. The distal protection system of the present invention can be designed as a rapid exchange system as shown in FIG. 11. The system contains a standard length lockable guidewire (5) with a ferrule (30) attached. The introducer catheter (45) extends from the proximal introducer (180) end to the guidewire access hole (185). The proximal introducer (180) can be a tube or solid elongated structure constructed out of a plastic, metal, or a composite. The lockable guidewire (5) travels generally parallel and along side of the proximal introducer (180) within the blood vessel. The intermediate introducer (190) extends from the guidewire access hole (185) to the introducer step (50). The distal introducer (15) extends from the introducer step (50) to the distal end (35) of the introducer catheter (45). The lockable guidewire (5) extends into the distal introducer (15) and travels through the intermediate introducer (190) and out the guidewire access hole (185). The distal coil (25) extends outside of the distal introducer (15). The filter assembly (10) is located in the distal introducer (15). The lockable guidewire (5) extends through the filter assembly (10) with the ferrule (30) located distal to the filter stop (65). The filter assembly (10) can have an ejector latch (60) that remains latched as described in FIG. 3 or that can unlatch upon ejection of the filter assembly (10) as shown in FIG. 4. To use the distal protection system of this embodiment, the standard length lockable guidewire (5) is advanced percutaneously distal to the site of the lesion. The proximal lockable guidewire (5) end is back fed through the distal introducer (15) distal end (35) through the filter assembly (10) and extends out of the guidewire access hole (185). The distal introducer (15) and filter assembly (10) are then delivered distal to the site of the lesion and the lockable guidewire (5) is retracted proximally until the ferrule (30) passes the ejector latch (60) and is located between the ejector latch (60) and the filter stop (65). The distal introducer (15) is then retracted while holding the lockable guidewire (5) in a steady position to release the filter assembly (10) into the blood vessel. Alternately, the lockable guidewire (5) can be advanced while maintaining the position of the introducer catheter (45). The introducer catheter (45) can then be removed proximally from the lockable guidewire (5) and an interventional therapeutic or diagnostic catheter that has a rapid exchange design can then be advanced over the standard length lockable guidewire (5). Following the therapeutic or diagnostic procedure the rapid exchange interventional catheter is removed and the rapid exchange introducer catheter (45) is reintroduced to the blood vessel over the lockable guidewire (5). The distal introducer (15) is advanced to the site of the filter assembly (10) and the lockable guidewire (5) is retracted such that the ferrule (30) interacts with the filter stop (65) to pull the filter assembly (10) into the distal introducer (15). The distal introducer (15) along with the filter assembly (10) containing embolic debris from the therapeutic or diagnostic procedure and lockable guidewire (5) are then withdrawn from the blood vessel.

Figure 12:
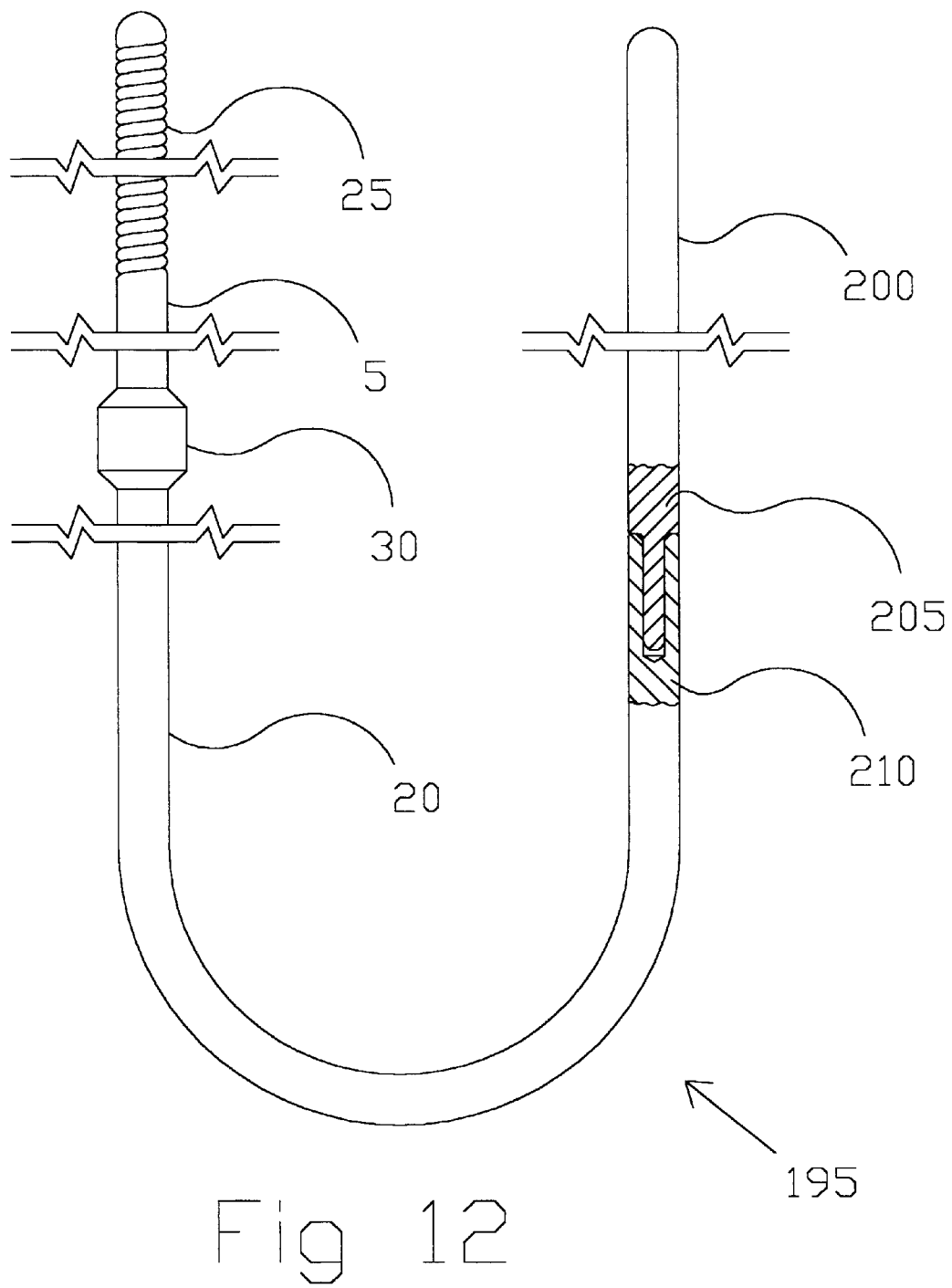
FIG. 12 is a partially sectioned plan view of an expandable lockable guidewire.

The interventionalist may wish to begin an interventional procedure by placing the distal protection system as described in FIG. 11 using an expandable lockable guidewire (195) of about 185–200 cm length as shown in FIG. 12. Following placement of the filter assembly (10) and removal of the introducer catheter (45) a rapid exchange type therapeutic or diagnostic catheter can be advanced to the site of the lesion using the lockable guidewire (5). However, if the physician wishes for any reason to use a standard over-the-wire therapeutic or diagnostic catheter, the lockable guidewire (5) of one embodiment can be adapted to allow a proximal extension (200) to be added to a guidewire to form an extended lockable guidewire (5) as shown in FIG. 12. The proximal adapter (205) can consist of a reduced diameter region that fits inside of a hole in the distal adapter (210). Once mated, the junction can be crimped to ensure that the proximal (205) and distal adapter (210) remain joined during the interventional procedure. It is understood that other adapter designs can be used to allow a proximal extension (200) to be added to the expandable lockable guidewire (195) without changing the present invention.

Figure 13A:
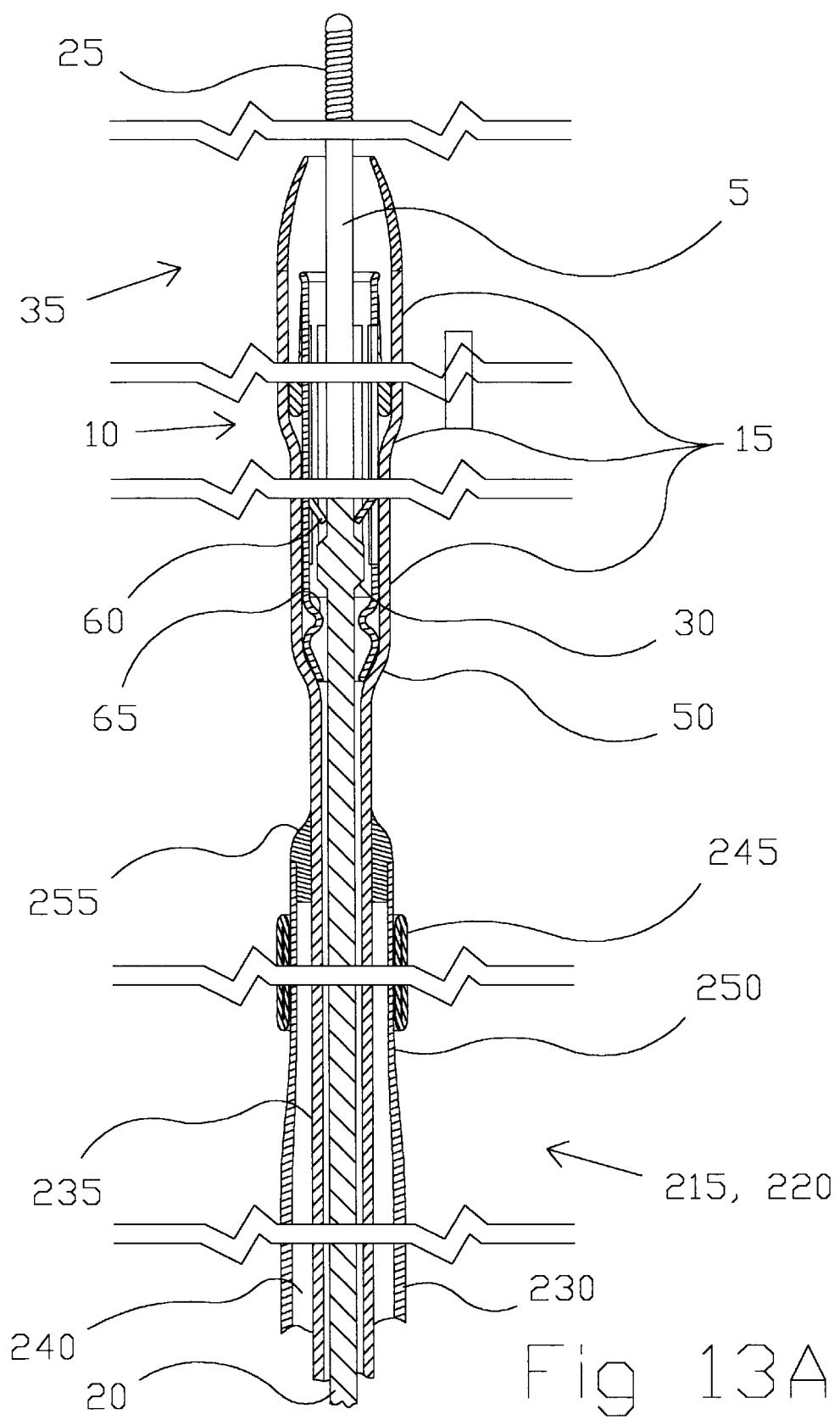
FIG. 13A is a detailed sectional view of an alternate embodiment of a distal protection and introducer system that includes an angioplasty balloon and is of a concentric design.
Figure 13B:
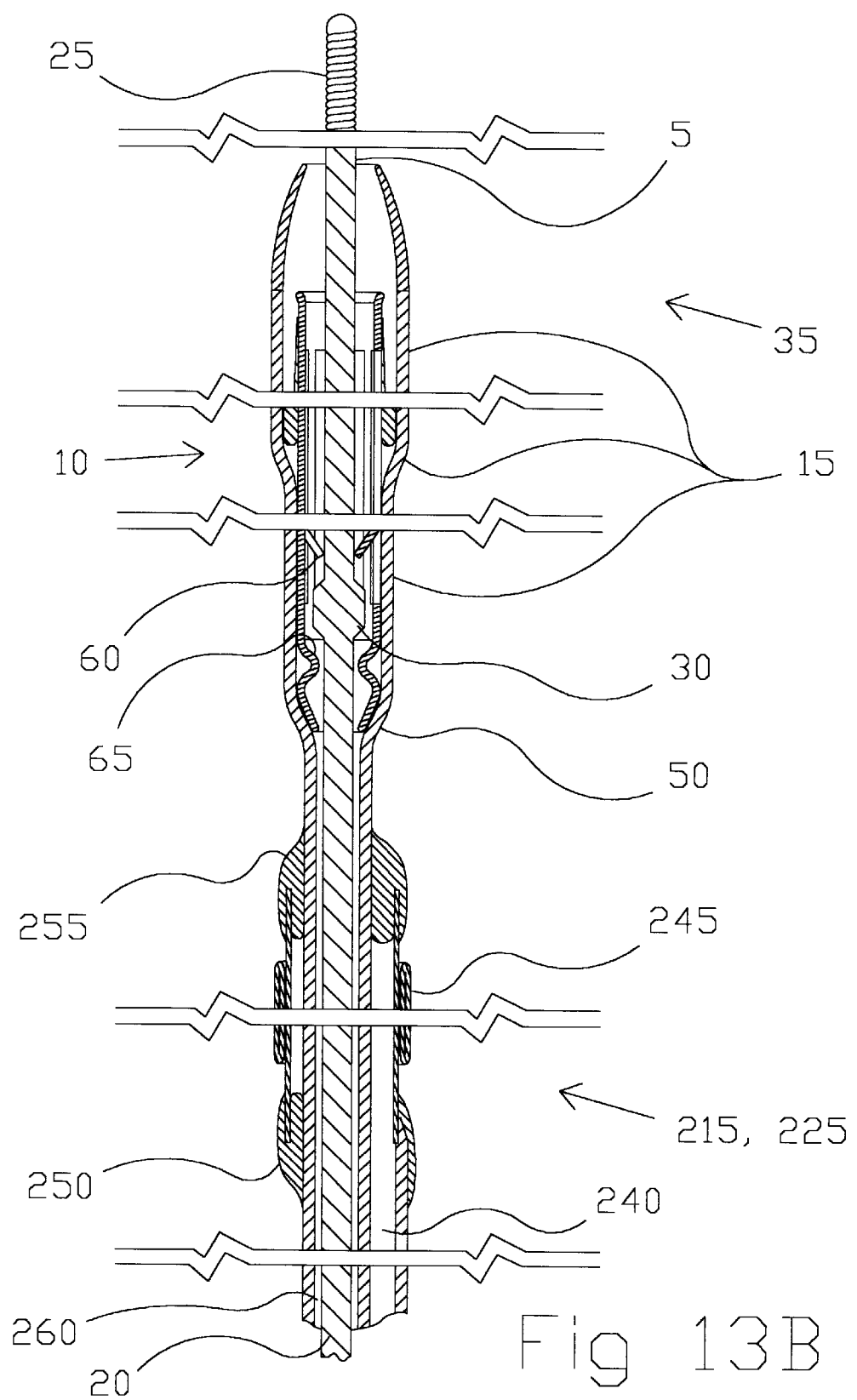
FIG. 13B is a detailed sectional view of an alternate embodiment of a distal protection and introducer system that includes an angioplasty balloon and is of a dual lumen design.

In FIGS. 13A and 13B, other embodiments of the present invention are shown having a portion of the distal introducer (15) attached either by joint or contiguously with the distal end (35) of an over-the-wire angioplasty catheter (215). In these embodiments the angioplasty catheter is serving as both a therapeutic catheter and an introducer catheter (45). Other interventional catheters such as atherectomy catheters or thrombectomy catheters can also serve as an introducer catheter (45) with a distal introducer (15) attached to the distal end (35) in a similar manner as described in this embodiment. The angioplasty catheter (215) shown in FIG. 13A is a concentric design (220) and the catheter shown in FIG. 13B is a dual lumen design (225). In FIG. 13A an inflation tube (230) surrounds the lockable guidewire tube (235) forming an annular inflation lumen (240) for the dilatation balloon (245); the lockable guidewire tube (235) runs within the inflation tube (230) and provides passage for the lockable guidewire (5). The dilatation balloon (245) makes a proximal attachment (250) either contiguously or by bonding to the inflation tube (230) and makes a distal attachment (255) to the lockable guidewire tube (235). The lockable guidewire tube (235) extends distally from the distal attachment (255) and is joined either contiguously or by a bond to the distal introducer (15). An introducer step (50) interfaces with the filter assembly (10) and prevents movement of the filter assembly (10) proximally. The lockable guidewire (5) extends through the filter assembly (10) and exits distal to the distal introducer (15). The lockable guidewire (5) has a flexible distal end (35) such as that provided by a distal coil (25). The ferrule (30) of the lockable guidewire (5) is shown in a latched condition between the filter stop (65) and the ejector latch (60) of the filter assembly (10). The filter assembly (10) can be the same as the embodiments described in FIGS. 3,4,6A–6B,7A–7B, 8A–8F, and 9A–9D and the reference numerals used in the filter assembly (10) of FIG. 13A are similar to those used in the previous embodiments.

In FIG. 13B one lumen of a duel lumen tubing forms the inflation lumen (240) for the dilatation balloon (245); the other forms (lumen contains) the lockable guidewire lumen (260). The dilatation balloon (245) is in fluid communication with the inflation lumen (240). The lockable guidewire lumen (260) extends distally from the distal attachment (255) of the dilatation balloon (245) and extends into the distal introducer (15). The distal introducer (15) has an introducer step (50) that interfaces with the filter assembly (10). The lockable guidewire (5) has a ferrule (30) that is shown in a latched condition between the filter stop (65) and the ejector latch (60) of the filter assembly (10). The lockable guidewire (5) has a flexible distal end (35) such as that provided by a distal coil (25). The filter assembly (10) of this embodiment can be the same as the filter assembly (10) shown in FIGS.3, 4, 6A–6B, 7A–7B, 8A–8F, and 9A–9D and the reference numerals used in the filter assembly (10) of FIG. 13B are similar to those used in the previous embodiments.

In one method of use for the distal protection system of FIGS. 13A and 13B the lockable guidewire (5) is backloaded into the angioplasty catheter (215) prior to percutaneous insertion into the vasculature. The ferrule (30) is positioned distal to the ejector latch (60) and the distal protection system is advanced into a guide catheter or other catheter and delivered to the coronary ostium or other appropriate location within the vasculature. The ferrule (30) of the lockable guidewire (5) can then be advanced further distal to the site of the lesion while maintaining the location of the distal introducer (15) further proximally either in the guide catheter or other location proximal to the lesion. The distal introducer (15) can then be advanced over the lockable guidewire (5) to a site distal to the lesion and further advanced while holding the lockable guidewire (5) stationary until the ferrule (30) has latched between the ejector latch (60) and the filter stop (65). Alternately, the lockable guidewire (5) could be retracted while maintaining the position of the distal introducer (15) stationary until the ferrule (30) has latched. The distal introducer (15) is then retracted while maintaining the position of the lockable guidewire (5) to eject the filter assembly (10) into the vasculature distal to the lesion. Alternately, the lockable guidewire (5) is advanced distally while maintaining the position of the distal introducer (15). The distal introducer (15) is further retracted such that the dilatation balloon (245) is positioned over the lesion site and angioplasty is performed. Stent placement can also be accomplished using this system if a stent is loaded on the outside of the dilatation balloon (245) and is balloon expanded into position within the vessel. Following balloon angioplasty, the distal introducer (15) can be advanced distally to the site of the filter assembly (10). The lockable guidewire (5) can be retracted proximally and the ferrule (30) will pull the filter assembly (10) and its collected embolic debris into the distal introducer (15). The distal protection system can then be removed from the vasculature. The lockable guidewire (5) used could be of a standard length if the interventionalist feels that the lesion will require a routine angioplasty procedure or it can be treated with direct stenting. If a possibility exists that an additional interventional catheter beyond the device shown in either FIGS. 13A and 13B may be required, then an expandable lockable guidewire (195) such as that shown in FIG. 12 may be used or an exchange length lockable guidewire (5) may be used.

Figure 14:
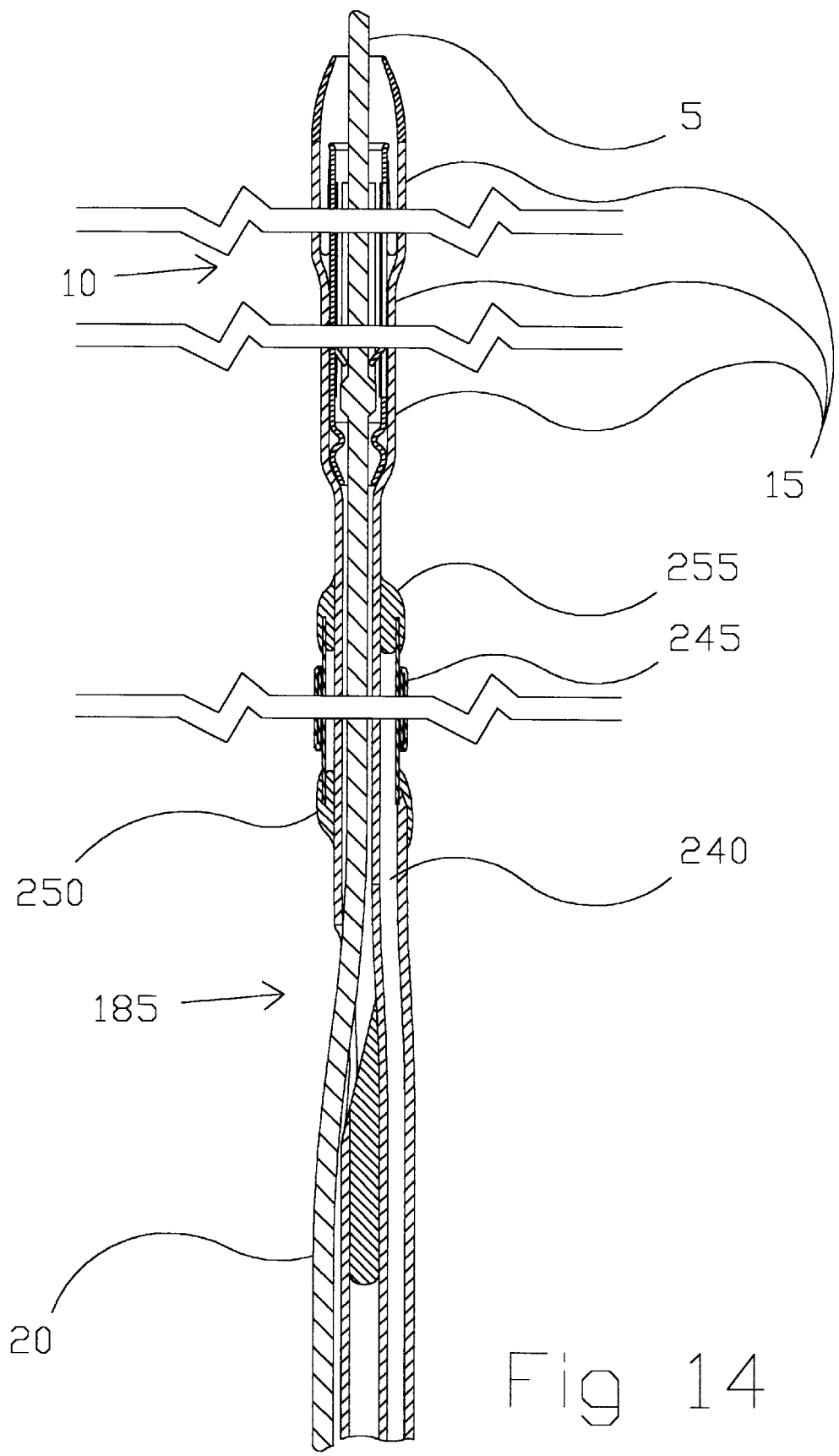
FIG. 14 is a detailed sectional view of an alternate embodiment of a distal protection and introducer system that includes an angioplasty balloon and is of a rapid exchange dual lumen design.

Another embodiment of the distal protection system is shown in FIG. 14. This embodiment is similar to the embodiment of FIG. 13B except that it is a rapid exchange distal protection system with angioplasty and stent placement capabilities. It is understood that the device of FIG. 13A could similarly be structured as a rapid exchange catheter by allowing the lockable guidewire tube (235) to exit the inflation tube (230) at a region that is close to and proximal to the dilatation balloon (245). In FIG. 14 a lockable guidewire access hole (185)(exit site) allows the lockable guidewire (5) to exit the lockable guidewire lumen (260) at a position proximal to the dilatation balloon (245). The distal introducer (15) and filter assembly (10) is similar to that described in FIG. 13B and the reference numerals are similar to those shown in FIG. 13B. The distal protection system of this embodiment allows the use of a standard length of lockable guidewire (5) or about 150–240 cm to be used to deliver the distal introducer (15) and filter assembly (10) distal to the lesion and to retrieve the filter assembly (10) following the therapeutic or diagnostic procedure. To use the device of this embodiment the lockable guidewire (5) is advanced distal to the site of the lesion. The distal portion of the rapid exchange catheter is advanced over the lockable guidewire (5) to the site of the lesion. The latching, ejection, and retrieval of the filter assembly (10) is the same as described in FIGS. 13A and 13B. Following the angioplasty procedure by the dilatation balloon (245) of this device, the distal introducer (15) can be removed from the vasculature while leaving the lockable guidewire (5) and filter assembly (10) in place across the lesion for other adjunctive interventional use such as stent placement. Following the completion of lesion treatment, the original distal introducer (15) can be introduced or another introducer catheter (45) with a distal introducer (15) such as that shown in the embodiment of FIG. 11 can be introduced over the lockable guidewire (5) and advanced to the site of the filter assembly (10). The filter assembly (10) can then be retracted into the distal introducer (15) and removed from the vasculature.

Various modifications can be made to the present invention without departing from the apparent scope hereof.

I claim:

1. A delivery system for delivering a distal protection filter assembly into the vasculature by an introducer for filtering embolic debris in flowing blood, the distal protection filter assembly being capable of extending from a smaller nondeployed state to a larger deployed state, said delivery system comprising;
   A. a guidewire having a locking means,
   B. an introducer that holds the distal protection filter assembly in the smaller nondeployed state,
   C. a stop means having the distal protection assembly attached thereto and preventing the passage of said locking means therethrough,
   D. an ejector means interacting with the distal protection filter assembly and providing for relative movement between the distal protection filter assembly and said introducer to eject the distal protection filter assembly from said introducer and into the vasculature allowing expansion of the distal protection filter to a larger deployed state.

2. The delivery system of claim 1 wherein said ejector means is an ejector latch that latches the distal protection filter assembly to said guidewire.

3. The delivery system of claim 2 wherein said ejector latch remains latched following introduction of said filter assembly into the vasculature.

4. The delivery system of claim 2 wherein said ejector latch has means to unlatch following introduction of said filter assembly into the vasculature.

5. The delivery system of claim 1 wherein said ejector means is an ejector tube that pushes the distal protection filter assembly out of said introducer.

6. The delivery system of claim 1 wherein said introducer comprises a stepped region having a dimension that is less than the dimension of the distal protection filter assembly.

7. The delivery system of claim 1 wherein said introducer is attached to the distal end of an interventional catheter.

8. The delivery system of claim 1 wherein said introducer is attached to the distal end of a guidewire tubing of an interventional catheter.

9. The delivery system of claim 1 wherein said introducer is attached to the distal end of a guidewire tubing on a dilatation catheter.

10. The delivery system of claim 9 wherein the dilatation catheter is an over-the-wire catheter.

11. The delivery system of claim 9 wherein the dilatation catheter is a rapid exchange catheter.

12. The delivery system of claim 1 wherein said introducer is an over-the-wire catheter.

13. The delivery system of claim 1 wherein said introducer is a rapid exchange catheter.

14. The delivery system of claim 1 wherein said guidewire is expandable in length.

15. The delivery system of claim 1 wherein said locking means comprises a ferrule.

16. The delivery system of claim 1 wherein said stop means is a narrowed region having the distal protection filter assembly attached thereto, said narrowed region having a minor dimension less than a major dimension of said locking means.

17. A delivery system for deploying and retrieving a distal protection filter assembly out of and back into an introducer from an initial smaller undeployed state to a larger deployed state and then to a smaller removable state into and out of the vasculature for filtering embolic debris out of blood that is flowing through the vasculature and removing the embolic debris captured by the distal protection filter assembly along with the distal protection filter assembly, said delivery system comprising;
   A. a guidewire having a latchable means near its distal end, said latchable means having a major dimension that is greater than the guidewire dimension,
   B. a stop means having a distal protection filter assembly attached thereto, said stop means having a minor dimension that is less than said guidewire latchable means major dimension,
   C. an ejector means for ejecting the distal protection filter assembly from the introducer, said ejector means having a radial dimension that is greater than the trunk diameter of said guidewire and less than the major radial dimension of the distal protection filter assembly.

18. A method of use for a delivery system for introduction of a distal protection filter assembly into the vasculature for filtering embolic debris in flowing blood, the distal protection filter assembly expanding from a smaller nondeployed state to a larger deployed state, the method comprising;
   A. advancing a guidewire having a locking means percutaneously distal to the site of a vascular lesion,
   B. advancing an introducer containing the distal protection filter assembly over the guidewire to a site distal to the vascular lesion,
   C. advancing the distal protection filter assembly with respect to said introducer into the vasculature with an ejector means that interacts with the distal protection filter assembly,
   D. retracting said introducer from the vasculature.

19. A method of use for a delivery system for removal of a distal protection filter assembly from the vasculature for removing embolic debris captured from flowing blood, the distal protection filter assembly contracting from a larger deployed state to a smaller nondeployed state, the method comprising;
   A. advancing an introducer over a guidewire having a locking means to the site of the distal protection filter assembly,
   B. retracting said guidewire and causing said locking means of said guidewire to interface with a stop means having the distal protection filter assembly being attached thereto,
   C. pulling at least a portion of the distal protection filter assembly into said introducer and removing said delivery system and the distal protection filter assembly from the vasculature.

20. A method of use for a delivery system for introduction of a distal protection filter assembly into the vasculature for filtering embolic debris in flowing blood, and performing an interventional procedure, the method comprising;
   A. advancing a guidewire having a locking means percutaneously distal to the site of a vascular lesion,
   B. advancing an interventional catheter having an introducer attached that contains the distal protection filter assembly over said guidewire to a site distal to the vascular lesion,
   C. advancing the distal protection filter assembly with respect to said introducer into the vasculature with an ejector means that interacts with the distal protection filter assembly,
   D. retracting said interventional catheter to the site of the lesion and performing an interventional procedure,
   E. advancing said interventional catheter with introducer attached thereto over said guidewire to the site of the distal protection filter assembly,
   F. retracting said guidewire and causing said locking means of said guidewire to interface with a stop means having the distal protection filter assembly being attached thereto,
   G. pulling at least a portion of the distal protection filter assembly into said introducer and removing said delivery system and the distal protection filter assembly from the vasculature.

\* \* \* \* \*